(12) United States Patent
Chou et al.

(10) Patent No.: US 12,405,216 B2
(45) Date of Patent: Sep. 2, 2025

(54) RAPID PATHOLOGY/CYTOLOGY WITHOUT WASH

(71) Applicant: Essenlix Corporation, Monmouth Junction, NJ (US)

(72) Inventors: Stephen Y. Chou, Princeton, NJ (US); Wei Ding, Princeton, NJ (US); Yu Sun, Basking Ridge, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

(21) Appl. No.: 17/606,973

(22) PCT Filed: Apr. 28, 2020

(86) PCT No.: PCT/US2020/030325
§ 371 (c)(1),
(2) Date: Oct. 27, 2021

(87) PCT Pub. No.: WO2020/223265
PCT Pub. Date: Nov. 5, 2020

(65) Prior Publication Data
US 2022/0136969 A1    May 5, 2022

Related U.S. Application Data

(60) Provisional application No. 62/844,701, filed on May 7, 2019, provisional application No. 62/839,767, filed on Apr. 28, 2019.

(51) Int. Cl.
*G01N 21/64* (2006.01)
*G01N 1/31* (2006.01)

(52) U.S. Cl.
CPC ......... *G01N 21/6428* (2013.01); *G01N 1/312* (2013.01); *G01N 2021/6439* (2013.01)

(58) Field of Classification Search
CPC .............. G01N 21/6428; G01N 1/312; G01N 2021/6439
USPC ........................................................ 435/5
See application file for complete search history.

(56) References Cited

U.S. PATENT DOCUMENTS

| | | | |
|---|---|---|---|
| 2007/0037138 A1* | 2/2007 | Winther | G01N 15/1468 435/7.1 |
| 2012/0122078 A1* | 5/2012 | Patterson | G01N 33/5091 435/5 |
| 2015/0065372 A1 | 3/2015 | Amir et al. | |
| 2018/0202903 A1* | 7/2018 | Chou | B01L 3/5055 |
| 2019/0128869 A1 | 5/2019 | Chou et al. | |

FOREIGN PATENT DOCUMENTS

WO    WO-2017027643 A1 *    2/2017    ............ B01L 3/5055

* cited by examiner

*Primary Examiner* — Jill A Warden
*Assistant Examiner* — Jacqueline Brazin

(57) ABSTRACT

Among other things, the disclosure of the present invention is related to make pathology and cytology faster, better and lower cost. The present invention also related to rapid intracellular assay.

29 Claims, 4 Drawing Sheets

RAPID PATHOLOGY/CYTOLOGY WITHOUT WASH

CROSS REFERENCING

This application is a National Stage entry (§ 371) application of International Application No. PCT/US20/30325, filed on Apr. 28, 2020, which claims the benefit of U.S. Provisional Application No. 62/839,767, filed on Apr. 28, 2019, and U.S. Provisional Application No. 62/844,701, filed on May 7, 2019, both of which applications are incorporated herein in their entireties for all purposes. The entire disclosure of any publication or patent document mentioned herein is entirely incorporated by reference.

FIELD

The disclosure of the present invention is related to improve pathology and cytology.

BACKGROUND

In biological and chemical assays (e.g. diagnostic testing), often it needs to stain and visualize analyte in biological samples quickly and simply. The current invention provides devices and methods for achieving these goals. There are needs to reduce the steps, time and cost in pathology and cytology. Among other things, the disclosure of the present invention is related to make pathology and cytomology faster, better and lower cost. The present invention also related to rapid intra-cellular assay.

SUMMARY OF THE INVENTION

One aspect of the present invention is to perform rapid pathology and cytology without washing. Particularly, the present invention a is related to devices and methods that perform assaying (i.e. detection and/or staining) of an analyte in a sample in one step without washing, short incubation time (less than a few minutes, or 60 seconds) and immediately ready for reading signals.

Another aspect of the present invention is to improve sample staining and imaging by placing a conformable plate with spacers of uniform height. The conformable plate can rapidly prepare and stain a tissue and allow the tissue being imaged without washing Another aspect of the present invention is to stain and image a tissue using a conformable plate with spacers of uniform height by pressing the tissue to a thickness much less than the initial thickness.

Another aspect of the present invention is to improve tissue imaging using conformable flexible plate (i.e. film) of uniform micro-spacers.

Another aspect of the present invention is to perform rapid homogenous intracellular assay that detect the analyte inside the cell, and that can be much more sensitive than the assays that detect the same analyte outside the cell in a sample.

In some embodiments, the present invention provides a method of staining a tissue, comprising placing on a bottom plate a slice of tissue to be stained, providing a flexible top plate having, on its surface, spacers with a uniform height of 100 um or less, depositing a stain solution either on the tissue surface or on the flexible top plate, and sandwiching the sample and the stain solution between the top flexible plate and the bottom plate and pressing them together, wherein the flexibility of the top flexible plate and the spacing between the spacer are selected to make the top flexible plate conform to the surface of the tissue.

In some embodiments, the present invention provides a method of rapidly analyzing the pathology or cytology of a sample without washing the sample, comprising providing a first plate and a second plate; each, on its surface, having a sample contact area for contacting a sample that contains or is suspected of containing a target tissue or cell, providing a staining solution that stains the target tissue or cell, sandwiching the sample and the stain solution between the first and the second plates to form a thin layer of thickness of 200 um or less, and after sandwiching the sample and the stain solution between the first and the second plates to form a thin layer of thickness of 200 um or less, and without washing the sample to remove stain solution from the sample, imaging the thin layer to observe the stained target tissue or cell, wherein the thickness of the thin layer and the concentration of the stain solution in the thin layer are selected to make, during the imaging, the stained target tissue or cell in the thin layer is distinguishable from the rest of thin layer.

In some embodiments, the present invention provides a kit for analyzing the pathology of a sample without wash, comprising a first plate and a second plate, each, on its surface, having a sample contact area for contacting a sample that contains or is suspected of containing a target tissue or cell, and a staining solution that stains the target tissue or cell, wherein the first and second plates sandwich the sample and the stain solution into a thin layer of thickness that is regulated by the distance between the two sample contact areas, wherein the thin layer is imaged by an imager without washing the sample to remove stain solution from the sample, and wherein the distance between the two sample contact areas and the concentration of the stain solution in the thin layer are selected to make, during the imaging, the stained target tissue or cell in the thin layer is distinguishable from the rest of thin layer.

In some embodiments, the present invention provides an apparatus for analyzing the pathology of a sample without washing the sample, comprising a first plate and a second plate; each, on its surface, having a sample contact area for contacting a sample that contains or is suspected of containing a target tissue or cell, a staining solution that stains the target tissue or cell, and an imager, wherein the first and second plates sandwich the sample and the stain solution into a thin layer of a thickness that is regulated by the distance between the two sample contact areas, wherein the imager images the thin layer without washing the sample to remove stain solution from the sample, and wherein the distance between the two sample contact areas and the concentration of the stain solution in the thin layer are selected to make, during the imaging, the stained target tissue or cell in the thin layer is distinguishable from the rest of thin layer.

In some embodiments, the present invention provides a method for a rapid homogenous detection of an analyte inside a membrane of a cell in a sample, comprising the steps of (a) providing a first plate and a second plate, each, on its surface, having a sample contact area for contacting a sample comprising a cell that contains or is suspected of containing an analyte inside the cell, (b) providing a detection probe that (i) specifically binds the analyte and (ii) is capable of emitting a light at a wavelength, (c) providing a permeabilization reagent that makes a membrane of the cell permeable to the detection probe, wherein without the permeabilization reagent the detection probe cannot permeate into the cell, (d) sandwiching the sample, the detection probe, and the permeabilization reagent between the first and second plates to form a thin layer of a thickness of 200 microns (um) or less, and (e) after the step (d) and without washing the sample to remove unbound detection probe, imaging the thin layer to detect the cell that has the analyte bound to the detection probe, wherein the thickness of the thin layer and the concentration of the detection probe in the thin layer are selected to make, in the thin layer, the signal from the location having the detection probe bound to the analyte inside the cell distinguishable from signals from the locations that do not have the cell during the imaging of step (e). In some embodiments, the imaging of step (e) is performed 300 seconds or less after sandwiching of step (d). In one embodiment, the method further comprises a step of quantifying (i) the cell that has an analyte inside the cell and (ii) the cell that does have an analyte inside the cell. In another embodiment, the method further comprises a step of quantifying (i) the cell that has an analyte inside the cell and (ii) the cell that does have an analyte inside the cell, and a step of quantifying the percentage of the cell having an analyte inside the cell relative to the total number of the cell. In yet another embodiment, the light emitted by the detection probe is fluorescence, and the method further comprises (i) measuring the fluorescence intensity of the cell having the analyte bound to the detection probe, (ii) measuring the number of the cells having the analyte bound to the detection probe, and (iii) calculating a total fluorescence intensity by multiplying the total number of cells having the analyte bound to the detection probe in a unit area and the average of the fluorescence intensity of the cell having the analyte bound to the detection probe.

In some embodiments, the present invention provides a method of rapidly preparing and staining a tissue with an initial thickness thicker than the final thickness, comprising providing a first plate and a second plate that are movable relative to each other, wherein the second plate has spacers of uniform heights on its surface, placing, on the first plate, a tissue sample that has a thickness thicker than the spacer height, depositing a staining solution on the first plate or on the tissue, wherein the staining solution stains the tissue sample, and placing the first plate on top of the tissue sample and pressing to two plates together to make the tissue sample to form a thin layer, wherein the final thickness of the tissue sample layer is less than the initial thickness of the tissue sample and is regulated by the spacers and the two plates.

In some embodiments, the present invention provides a method of improving an imaging of a tissue surface, comprising providing a flexible plate, proving a spacers of uniform height, placing the spacer and the flexible plate on top of a tissue to be imaged, wherein the height of the spacer regulate the distance between the plate and the tissue, and wherein the spacer height is 50 um (micron) or less. In one embodiment, the uniform height is selected between 2 um to 20 um. In another embodiment, the uniform height is 10 um.

In some embodiments, the first and second plates are movable relative to each other into different configurations, including an open configuration and a closed configuration, wherein the plate or the plates have spacers of uniform height on its surface, wherein in an open configuration, the two plates are completely or partially separated apart, the spacing between the plates is not regulated by the spacers, and wherein in a closed configuration, the thickness of the thin layer is regulated by the plates, and the spacers, and has an average distance between the sample surface and the second plate surface is equal or less than 200 μm.

In some embodiments, the device, kit, and method further comprise the spacers that regulate the distance between the first plate and the second plate.

In some embodiments, the thickness of the thin layer is selected to make some of the cell having no overlap or significant overlap with other cells in the thin layer.

In some embodiments, the permeabilization reagent is coated on the surface of the plate or the plates.

In some embodiments, the permeabilization reagent is introduced to the sample before the sample and the permeabilization reagent are sandwiched between the two plates.

In some embodiment, the plate further has a dry stain reagent coated on its surface, and wherein the staining solution is a transfer liquid that transfers the dry stain agent into the sample.

In some embodiments, the stain solution is introduced to the sample before the sample and the permeabilization reagent are sandwiched between the two plates.

In one aspect, the present disclosure provides a method comprising obtaining a plate comprising one or more spacers fixed to a sample contact area on a surface thereof. In certain embodiments, the method comprises depositing a liquid onto at least one of (i) the sample contact area and (ii) a surface to be imaged. In certain embodiments, the method comprises contacting the one or more spacers with the surface to be imaged, thereby compressing at least a portion of the liquid into a layer of substantially uniform thickness confined by the plate and the surface to be imaged, wherein the uniform thickness of the layer is regulated by the height of the one or more spacers, and wherein the height of the one or more spacers is less than about 250 microns (um). In certain embodiments, the method comprises imaging the surface to be imaged.

In another aspect, the present disclosure provides a method comprises obtaining a first plate and a second plate, each comprising one or more spacers fixed to a sample contact area on a surface thereof. In certain embodiments, the method comprises depositing a staining liquid onto at least one of (i) the sample contact area of the first plate and (ii) a surface to be imaged. In certain embodiments, the method comprises contacting the one or more spacers of the first plate with the surface to be imaged. In certain embodiments, the method comprises, after a predetermined period of time, separating the first plate from the surface to be imaged. In certain embodiments, the method comprises depositing an imaging liquid onto at least one of (i) the sample contact area of the second plate and (ii) the surface to be imaged. In certain embodiments, the method comprises contacting the one or more spacers of the second plate with the surface to be imaged, thereby compressing at least a portion of the imaging liquid into a layer of substantially uniform thickness confined by the first plate and the surface to be imaged, wherein the uniform thickness of the layer is regulated by the height of the one or more spacers, and wherein the height of the one or more spacers is less than about 250 um. In certain embodiments, the method comprises imaging the surface to be imaged.

In one aspect, the present disclosure provides a device for analyzing a tissue sample, comprising a first plate; a second plate; a plurality of spacers; and a staining liquid, wherein the plates are movable relative to each other into different configurations; one or both plates are flexible; each of the plates has, on its respective inner surface, a sample contact area for contacting a staining liquid and/or a tissue sample contains or suspected of containing a target analyte; one or both of the plates comprise the spacers that are fixed with a respective plate; the spacers have a predetermined substantially uniform height and a predetermined inter-spacer distance; and at least one of the spacers is inside the sample contact area; wherein one of the configurations is an open configuration, in which: the two plates are partially or entirely separated apart, the spacing between the plates is not regulated by the spacers, and the staining liquid and the sample are deposited on one or both of the plates; and wherein another of the configurations is a closed configuration, which is configured after the deposition of the staining liquid and the sample in the open configuration, and in the closed configuration: at least part of the sample is between the two plates and a layer of at least part of staining liquid is between the at least part of the sample and the second plate, wherein the thickness of the at least part of staining liquid layer is regulated by the plates, the sample, and the spacers, and has an average distance between the sample surface and the second plate surface is equal to or less than 250 µm with a small variation.

In one aspect, the present disclosure provides a device for analyzing a tissue sample, comprising a first plate; a second plate; a plurality of spacers; a transfer solution; and a staining liquid, wherein the plates are movable relative to each other into different configurations; one or both plates are flexible; each of the plates has, on its respective inner surface, a sample contact area for contacting a transfer solution and/or a tissue sample contains or suspected of containing a target analyte; one or both of the plates comprise a stain agent that is coated on the respective sample contact area and configured to, upon contacting the transfer solution, be dissolved in the transfer solution and stain the tissue sample; one or both of the plates comprise the spacers that are fixed with a respective plate; the spacers have a predetermined substantially uniform height and a predetermined inter-spacer distance; and at least one of the spacers is inside the sample contact area; wherein one of the configurations is an open configuration, in which: the two plates are partially or entirely separated apart, the spacing between the plates is not regulated by the spacers, and the staining liquid and the sample are deposited on one or both of the plates; and wherein another of the configurations is a closed configuration, which is configured after the deposition of the staining liquid and the sample in the open configuration, and in the closed configuration: at least part of the sample is between the two plates and a layer of at least part of transfer solution is between the at least part of the sample and the second plate, wherein the thickness of the at least part of transfer solution layer is regulated by the plates, the sample, and the spacers, and has an average distance between the sample surface and the second plate surface is equal to or less than 250 µm with a small variation.

In one aspect, the present disclosure provides a method for analyzing a tissue sample, comprising the steps of providing a tissue sample contains or suspected of containing a target analyte; providing a staining liquid; providing a first plate, a second plate, and spacers, wherein the plates are movable relative to each other into different configurations, one or both plates are flexible; each of the plates has, on its respective inner surface, a sample contact area for contacting the staining liquid and/or the tissue sample; one or both of the plates comprise the spacers that are fixed with a respective plate; the spacers have a predetermined substantially uniform height and a predetermined inter-spacer distance; and at least one of the spacers is inside the sample contact area; depositing the staining liquid and the tissue sample on one or both of the plates when the plates are in an open configuration, wherein the open configuration is a configuration in which the two plates are partially or entirely separated apart, the spacing between the two plates is not regulated by the spacers, and the sample and the staining liquid are deposited on one or both of the plates; bringing the two plates together and pressing the plates into a closed configuration, wherein the pressing comprises conformable pressing, either in parallel or sequentially, an area of at least one of the plates to press the plates together to the closed configuration, wherein the conformable pressing generates a substantially uniform pressure on the plates over the at least part of the sample, and the pressing spreads the at least part of the sample laterally between the inner surfaces of the plates; and wherein another of the configurations is the closed configuration, which is configured after the deposition of the staining liquid and the sample in the open configuration, and in the closed configuration: at least part of the sample is between the two plates and a layer of at least part of staining liquid is between the at least part of the sample and the second plate, wherein the thickness of the at least part of staining liquid layer is regulated by the plates, the sample, and the spacers, and has an average distance between the sample surface and the second plate surface is equal to or less than 250 µm with a small variation; and analyzing the target analyte when the plates are in the closed configuration.

In one aspect, the present disclosure provides a method for analyzing a tissue sample, comprising the steps of obtaining a tissue sample contains or suspected of containing a target analyte and a transfer solution; obtaining a first plate, a second plate, and spacers, wherein the plates are movable relative to each other into different configurations; one or both plates are flexible; each of the plates has, on its respective inner surface, a sample contact area for contacting a staining liquid and/or a tissue sample suspected of containing a target analyte; one or both of the plates comprise stain agents that are coated on the respective sample contact area and configured to, upon contacting a transfer solution, be dissolved in the transfer solution and stain the tissue sample; one or both of the plates comprise the spacers that are fixed with a respective plate; the spacers have a predetermined substantially uniform height and a predetermined inter-spacer distance; and at least one of the spacers is inside the sample contact area; depositing the staining liquid and the tissue sample on one or both of the plates when the plates are in an open configuration, wherein the open configuration is a configuration in which the two plates are partially or entirely separated apart, the spacing between the two plates is not regulated by the spacers, and the sample and the staining liquid are deposited on one or both of the plates; bringing the two plates together and pressing the plates into a closed configuration, wherein the pressing comprises conformable pressing, either in parallel or sequentially, an area of at least one of the plates to press the plates together to the closed configuration, wherein the conformable pressing generates a substantially uniform pressure on the plates over the at least part of the sample, and the pressing spreads the at least part of the sample laterally between the inner surfaces of the plates; and wherein another of the configurations is the closed configuration, which is configured after the deposition of the staining liquid and the sample in the open configuration, and in the closed configuration: at least part of the sample is between the two plates and a layer of at least part of staining liquid is between the at least part of the sample and the second plate, wherein the thickness of the at least part of staining liquid layer is regulated by the plates, the sample, and the spacers, and has an average distance between the sample surface and the second plate surface is equal to or less than 250 µm with a small variation; and analyzing the target analyte when the plates are in the closed configuration.

In one aspect, the present disclosure provides a method for analyzing a tissue sample, comprising the steps of providing a tissue sample contains or suspected of containing a target analyte; providing a transfer solution and a stain agent; providing a first plate, a second plate, and spacers, wherein the plates are movable relative to each other into different configurations; one or both plates are flexible; each of the plates has, on its respective inner surface, a sample contact area for contacting the tissue sample; one or both of the plates comprise a stain agent that are coated on the respective sample contact area and configured to, upon contacting a transfer solution, be dissolved in the transfer solution to form a staining liquid and stain the tissue sample; one or both of the plates comprise the spacers that are fixed with a respective plate; the spacers have a predetermined substantially uniform height and a predetermined inter-spacer distance; and at least one of the spacers is inside the sample contact area; depositing the tissue sample on one or both of the plates when the plates are in an open configuration, wherein the open configuration is a configuration in which the two plates are partially or entirely separated apart, the spacing between the two plates is not regulated by the spacers, and the sample and the staining liquid are deposited on one or both of the plates; bringing the two plates together and pressing the plates into a closed configuration, wherein the pressing comprises conformable pressing, either in parallel or sequentially, an area of at least one of the plates to press the plates together to the closed configuration, wherein the conformable pressing generates a substantially uniform pressure on the plates over the at least part of the sample, and the pressing spreads the at least part of the sample laterally between the inner surfaces of the plates; and wherein another of the configurations is the closed configuration, which is configured after the deposition of the staining liquid and the sample in the open configuration, and in the closed configuration at least part of the sample is between the two plates and a layer of at least part of staining liquid is between the at least part of the sample and the second plate, wherein the thickness of the at least part of staining liquid is regulated by the plates, the sample, and the spacers, and has an average distance between the sample surface and the second plate surface is equal to or less than 250 µm with a small variation; and without washing, analyzing the target analyte when the plates are in the closed configuration.

In one aspect, the present disclosure provides, a system for analyzing a tissue sample, comprising the device of any embodiment of the present disclosure; and a detector configured to detecting signals of the target analyte in the layer of uniform thickness.

In one aspect, the present disclosure provides a smartphone system for tissue analysis assay, comprising the device of any embodiment of the present disclosure; and a mobile communication device that comprises one or a plurality of cameras for detecting and/or imaging the sample, electronics, signal processors, hardware and software for receiving and/or processing the detected signal and/or the image of the sample and for remote communication; and an adaptor that is configured to accommodate the device that is in the closed configuration and be engageable to the mobile communication device, wherein when engaged with the mobile communication device, the adaptor is configured to facilitate the detection and/or imaging of the target analyte in the sample at the closed configuration.

The device, system, smartphone system or method of any embodiment of the present disclosure, wherein one or both of the plates is configured such that the sample can be dried thereon at the open configuration, and wherein the sample comprises bodily fluid selected from the group consisting of amniotic fluid, aqueous humour, vitreous humour, blood, breast milk, cerebrospinal fluid (CSF), cerumen (earwax), chyle, chime, endolymph, perilymph, feces, breath, gastric acid, gastric juice, lymph, mucus, pericardial fluid, peritoneal fluid, pleural fluid, pus, rheum, saliva, exhaled breath condensates, sebum, semen, sputum, sweat, synovial fluid, tears, vomit, urine, and any combination thereof.

The device, system, smartphone system or method of embodiment of the present disclosure, wherein the blood is whole blood, fractionated blood, plasma or serum.

The device, system, smartphone system or method of embodiment of the present disclosure, wherein the mucus is nasal drainage or phlegm.

The device, system, smartphone system or method of any embodiment of the present disclosure, wherein the staining liquid has a viscosity in the range of 0.1 to 3.5 mPa S.

The device, system, smartphone system or method of any embodiment of the present disclosure, wherein the sample contact area of one or both of the plates is configured such that the sample is dried thereon on one or both plates at the open configuration, and wherein the sample comprises blood smear.

The device, system, smartphone system or method of any embodiment of the present disclosure, wherein the sample contact area of one or both of the plates is adhesive to the sample, and wherein the sample is a tissue section having a thickness in the range of 1-200 µm.

The device, system, smartphone system or method of any embodiment of the present disclosure, wherein the sample is paraffin-embedded.

The device, system, smartphone system or method of any embodiment of the present disclosure, wherein the sample is fixed.

The device, system, smartphone system or method of any embodiment of the present disclosure, wherein the staining liquid comprises a fixative capable of fixing the sample.

The device, system, smartphone system or method of any embodiment of the present disclosure, wherein the staining liquid comprises a blocking agent, wherein the blocking agent is configured to disable non-specific endogenous species in the sample to react with detection agents that are used to specifically label the target analyte.

The device, system, smartphone system or method of any embodiment of the present disclosure, wherein the staining liquid comprises a deparaffinizing agent capable of removing paraffin in the sample.

The device, system, smartphone system or method of any embodiment of the present disclosure, wherein the staining liquid comprises a permeabilizing agent capable of permeabilizing cells in the tissue sample that contain the target analyte.

The device, system, smartphone system or method of any embodiment of the present disclosure, wherein the staining liquid comprises an antigen retrieval agent capable of facilitating retrieval of antigen.

The device, system, smartphone system or method of any embodiment of the present disclosure, wherein the staining liquid comprises a detection agent that specifically label the target analyte in the sample.

The device, system, smartphone system or method of any embodiment of the present disclosure, wherein the sample contact area of one or both plates comprise a storage site that contains a blocking agent, wherein the blocking agent is configured to disable non-specific endogenous species in the sample to react with the detection agent that is used to specifically label the target analyte.

The device, system, smartphone system or method of any embodiment of the present disclosure, wherein the sample contact area of one or both plates comprise a storage site that contains a deparaffinizing agent capable of removing paraffin in the sample.

The device, system, smartphone system or method of any embodiment of the present disclosure, wherein the sample contact area of one or both plates comprise a storage site that contains a permeabilizing agent capable of permeabilizing cells in the tissue sample that contain the target analyte.

The device, system, smartphone system or method of any embodiment of the present disclosure, wherein the sample contact area of one or both plates comprise a storage site that contains an antigen retrieval agent capable of facilitating retrieval of antigen.

The device, system, smartphone system or method of any embodiment of the present disclosure, wherein the sample contact area of one or both plates comprise a storage site that contains a detection agent that specifically label the target analyte in the sample.

The device, system, smartphone system or method of any embodiment of the present disclosure, wherein the detection agent comprises a compound selected from the group consisting of: Acid fuchsin, Alcian blue 8 GX, Alizarin red S, Aniline blue WS, Auramine O, Azocarmine B, Azocarmine G, Azure A, Azure B, Azure C, Basic fuchsine, Bismarck brown Y, Brilliant cresyl blue, Brilliant green, Carmine, Chlorazol black E, Congo red, C.I. Cresyl violet, Crystal violet, Darrow red, Eosin B, Eosin Y, Erythrosin, Ethyl eosin, Ethyl green, Fast green F C F, Fluorescein Isothiocyanate, Giemsa Stain, Hematoxylin, Hematoxylin & Eosin, Indigo carmine, Janus green B, Jenner stain 1899, Light green SF, Malachite green, Martius yellow, Methyl orange, Methyl violet 2B, Methylene blue, Methylene blue, Methylene violet, (Bernthsen), Neutral red, Nigrosin, Nile blue A, Nuclear fast red, Oil Red, Orange G, Orange II, Orcein, Pararosaniline, Phloxin B, Protargol S, Pyronine B, Pyronine, Resazurin, Rose Bengal, Safranine O, Sudan black B, Sudan III, Sudan IV, Tetrachrome stain (MacNeal), Thionine, Toluidine blue, Weigert, Wright stain, and any combination thereof.

The device, system, smartphone system or method of any embodiment of the present disclosure, wherein one or both of the plates further comprise, on the respective sample contact area, a cell viability dye selected from the group consisting of: Propidium Iodide, 7-AAD, Trypan blue, Calcein Violet AM, Calcein AM, Fixable Viability Dyes, SYTO9 and other nucleic acid dyes, Resazurin and Formazan (MTT/XTT) and other mitochondrial dyes, and any combination thereof.

The device, system, smartphone system or method of any embodiment of the present disclosure, wherein the detection agent comprises an antibody configured to specifically bind to the target analyte in the sample.

The device, system, smartphone system or method of any prior claim, wherein the detection agent comprises an oligonucleotide probe configured to specifically bind to DNA and/or RNA in the sample.

The device, system, smartphone system or method of any embodiment of the present disclosure, wherein the detection agent is labeled with a reporter molecule, wherein the reporter molecule is configured to provide a detectable signal to be read and analyzed.

The device, system, smartphone system or method of embodiment of the present disclosure, wherein the signal is selected from the group consisting of luminescence selected from photoluminescence, electroluminescence, and electrochemiluminescence, light absorption, reflection, transmission, diffraction, scattering, or diffusion, surface Raman scattering, electrical impedance selected from resistance, capacitance, and inductance, magnetic relaxivity and a combination thereof.

The device, system, smartphone system or method of any embodiment of the present disclosure, wherein the sample contact area of one or both of the plates comprise a binding site that contains a capture agent, wherein the capture agent is configured to bind to the target analyte on the surface of cells in the sample and immobilize the cells.

The method of any embodiment of the present disclosure, wherein the depositing step further comprises the steps of depositing and drying the sample on one or both of the plates before depositing the remaining of the staining liquid on top of the dried sample, and wherein the sample comprises a blood smear that is dried on one or both plates.

The method of any embodiment of the present disclosure, wherein the depositing step further comprises the steps of depositing and attaching the sample to one or both of the plates before depositing the staining liquid on top of the sample, wherein the sample contact area of one or both of the plates is adhesive to the sample, and wherein the sample is a tissue section having a thickness in the range of 1-200 □m.

The method of any embodiment of the present disclosure, before the analyzing step (e), further comprising: incubating the sample at the closed configuration for a period of time that is longer than the time it takes for the detection agent to diffuse across the layer of uniform thickness and the sample.

The method of any embodiment of the present disclosure, before the analyzing step (e), further comprising the step of incubating the sample at the closed configuration at a predetermined temperature in the range of 30-75° C.

The method of any embodiment of the present disclosure, wherein the staining liquid comprises the transfer solution.

The smartphone system of any embodiment of the present disclosure, wherein the mobile communication device is configured to communicate test results to a medical professional, a medical facility or an insurance company.

The smartphone system of any embodiment of the present disclosure, wherein the mobile communication device is further configured to communicate information on the subject with the medical professional, medical facility or insurance company.

The smartphone system of any embodiment of the present disclosure, wherein the mobile communication device is configured to receive a prescription, diagnosis or a recommendation from a medical professional.

The smartphone system of any embodiment of the present disclosure, wherein the mobile communication device communicates with the remote location via a WIFI or cellular network.

The smartphone system of any embodiment of the present disclosure, wherein the mobile communication device is a mobile phone.

The device, system, smartphone system or method of any embodiment of the present disclosure, wherein the pressing is performed by a human hand.

The device, system, smartphone system or method of any embodiment of the present disclosure, wherein at least a portion of the inner surface of one plate or both plates is hydrophilic.

The device, system, smartphone system or method of any embodiment of the present disclosure, wherein the inter spacer distance is periodic.

The device, system, smartphone system or method of any embodiment of the present disclosure, wherein the sample is a deposition directly from a subject to the plate without using any transferring devices.

The device, system, smartphone system or method of any embodiment of the present disclosure, wherein after the sample deformation at a closed configuration, the sample maintains the same final sample thickness, when some or all of the compressing forces are removed.

The device, system, smartphone system or method of any embodiment of the present disclosure, wherein the spacers have pillar shape and nearly uniform cross-section.

The device, system, smartphone system or method of any embodiment of the present disclosure, wherein the inter spacer distance (SD) is equal or less than about 120 μm (micrometer).

The device, system, smartphone system or method of any embodiment of the present disclosure, wherein the inter spacer distance (SD) is equal or less than about 100 μm (micrometer).

The device, system, smartphone system or method of any embodiment of the present disclosure, wherein the fourth power of the inter-spacer-distance (ISD) divided by the thickness (h) and the Young's modulus (E) of the flexible plate ($ISD^4/(hE)$) is $5 \times 10^6$ μm$^3$/GPa or less.

The device, system, smartphone system or method of any embodiment of the present disclosure, wherein the fourth power of the inter-spacer-distance (ISD) divided by the thickness (h) and the Young's modulus (E) of the flexible plate ($ISD^4/(hE)$) is $5 \times 10^5$ μm$^3$/GPa or less.

The device, system, smartphone system or method of any embodiment of the present disclosure, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

The device, system, smartphone system or method of any embodiment of the present disclosure, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate ($ISD^4/(hE)$) is $5 \times 10^6$ μm$^3$/GPa or less.

The device, system, smartphone system or method of any embodiment of the present disclosure, wherein the ratio of the inter-spacing distance of the spacers to the average width of the spacer is 2 or larger, and the filling factor of the spacers multiplied by the Young's modulus of the spacers is 2 MPa or larger.

The device, kit, system, smartphone system, and method of any embodiment of the present disclosure, wherein the target analytes is a protein, peptide, nucleic acid, synthetic compound, or an inorganic compound.

The device, system, smartphone system, and method of any embodiment of the present disclosure, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

The device, system, smartphone system, and method of any embodiment of the present disclosure, wherein the spacers have a shape of pillars and a ratio of the width to the height of the pillar is equal or larger than one.

The device, system, smartphone system or method of any embodiment of the present disclosure, wherein the sample that is deposited on one or both of the plates has an unknown volume.

The device, system, smartphone system, and method of any embodiment of the present disclosure, wherein the spacers have a shape of pillar, and the pillar has substantially uniform cross-section.

The device, system, smartphone system, and method of any embodiment of the present disclosure, wherein the samples are for the detection, purification and quantification of chemical compounds or biomolecules that correlates with the stage of certain diseases.

The device, system, smartphone system, and method of any embodiment of the present disclosure, wherein the sample is related to infectious and parasitic disease, injuries, cardiovascular disease, cancer, mental disorders, neuropsychiatric disorders, pulmonary diseases, renal diseases, and other and organic diseases.

The device, system, smartphone system, and method of any embodiment of the present disclosure, wherein the samples are related to the detection, purification and quantification of microorganism.

The device, system, smartphone system, and method of any embodiment of the present disclosure, wherein the samples is related to a virus, fungus and bacterium from environment, e.g., water, soil, or biological samples.

The device, system, smartphone system, and method of any embodiment of the present disclosure, wherein the samples is related to the detection, quantification of chemical compounds or biological samples that pose hazard to food safety or national security, e.g. toxic waste, anthrax.

The device, system, smartphone system, and method of any embodiment of the present disclosure, wherein the samples are related to quantification of vital parameters in medical or physiological monitor.

The device, system, smartphone system, and method of any embodiment of the present disclosure, wherein the samples are related to glucose, blood, oxygen level, total blood count.

The device, system, smartphone system, and method of any embodiment of the present disclosure, wherein the samples are related to the detection and quantification of specific DNA or RNA from bio-samples.

The device, system, smartphone system, and method of any embodiment of the present disclosure, wherein the samples are related to the sequencing and comparing of genetic sequences in DNA in the chromosomes and mitochondria for genome analysis.

The device, system, smartphone system, and method of any embodiment of the present disclosure, wherein the samples are related to detect reaction products, e.g., during synthesis or purification of pharmaceuticals.

The device, system, smartphone system, and method of any embodiment of the present disclosure, wherein the samples are cells, tissues, bodily fluids, and stool.

The device, system, smartphone system, and method of any embodiment of the present disclosure, wherein the sample is the sample in the detection of proteins, peptides, nucleic acids, synthetic compounds, inorganic compounds.

The device, system, smartphone system, and method of any embodiment of the present disclosure, wherein the sample is the sample in the fields of human, veterinary, agriculture, foods, environments, and drug testing.

The device, system, smartphone system or method of any embodiment of the present disclosure, wherein the sample is a biological sample is selected from blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk, exhaled condensate nasopharyngeal wash, nasal swab, throat swab, stool samples, hair, finger nail, ear wax, breath, connective tissue, muscle tissue, nervous tissue, epithelial tissue, cartilage, cancerous sample, and bone.

BRIEF DESCRIPTION OF THE DRAWINGS

A skilled artisan will understand that the drawings, described below, are for illustration purposes only. The drawings are not intended to limit the scope of the present teachings in any way. The drawings are not entirely in scale. In the figures that present experimental data points, the lines that connect the data points are for guiding a viewing of the data only and have no other means.

DETAILED DESCRIPTION OF EXEMPLARY EMBODIMENTS

Figure 1:
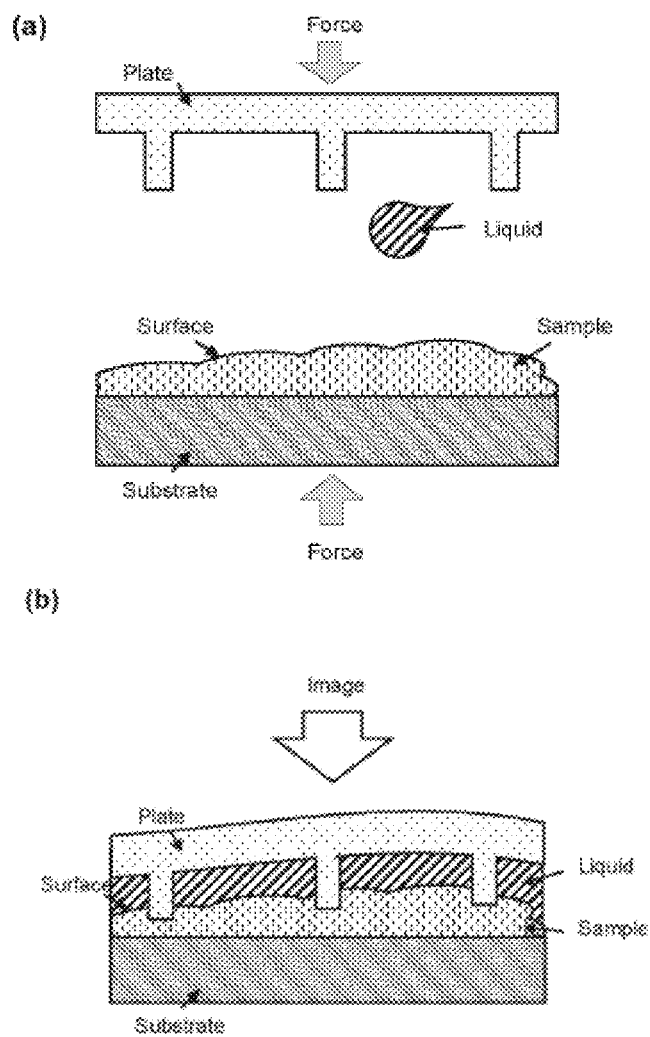
FIG. 1 illustrates an embodiment of the present disclosure, in which a conformable plate comprising spacers conforms to a shape of the surface of a sample.

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present disclosure.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

Definitions

The term "present disclosure" and "present invention" are interchangeable.

The term "FAST" (all in capital letters) means the "fast staining" of the present invention, which includes, but not limited to, all fast staining devices and/or methods described by the present invention. The terms "X-Path" and "FAST" are interchangeable.

The terms "perform, using a Q-Card, an assay (including staining in pathology) without using any wash" and "perform, using a Q-Card, an assay (including staining in pathology) wash-free" are interchangeable.

The terms "in a closed configuration" and "at a closed configuration" for the plates of the Q-Card are interchangeable.

The terms "analyte" and "biomarker" are interchangeable

The term "permeabilizing" a cell refers make the cell to allow large molecules like antibodies and/or nucleic acid to get inside the cell.

The term "multiplexing" is the use of multiple probes.

The term "staining solution" and "staining liquid" are interchangeable.

The term "inner surface" of the first and second plates is the surfaces that are facing each other in a closed configuration.

The terms "specific binding" and "selective binding" refer to the ability of a capture agent/detection agent to preferentially bind to a particular target molecule that is present in a heterogeneous mixture of different target molecule. A specific or selective binding interaction will discriminate between desirable (e.g., active) and undesirable (e.g., inactive) target molecules in a sample, typically more than about 10 to 100-fold or more (e.g., more than about 1000- or 10,000-fold).

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "a cell" includes a single cell and multiple cells.

1. Rapid Pathology and Cytology without Washing

According to one embodiment of the present invention, a method of stain a tissue, comprising:
 (a) placing on a bottom plate a slice of tissue to be stained;
 (b) providing a flexible top plate having, on its surface, spacers with a uniform height of 100 um or less;
 (c) depositing a stain solution either on the tissue surface or on the flexible top plate; and
 (d) sandwiching the sample and the stain solution between the top flexible plate and the bottom plate and pressing them together;
 wherein the flexibility of the top flexible plate and the spacing between the spacer are selected to make the top flexible plate conform to the surface of the tissue.

In another embodiment, a method of rapidly analyzing the pathology or cytology of a sample without wash, comprising:
 (e) providing a first plate and a second plate; each, on its surface, having a sample contact area for contacting a sample that contains or is suspected of containing a target tissue or cell;
 (f) providing a staining solution that stains the target tissue or cell;
 (g) sandwiching the sample and the stain solution between the first and the second plates to form a thin layer of thickness of 200 um or less; and
 (h) after step (c) and without washing the sample to remove stain solution from the sample, imaging the thin layer to observe the stained target tissue or cell;
 wherein the thickness of the thin layer and the concentration of the stain solution in the thin layer are selected to make, during the imaging, the stained target tissue or cell in the thin layer is distinguishable from the rest of thin layer.

In some embodiments, a kit for analyzing the pathology of a sample without wash, comprising:
 (a) a first plate and a second plate; each, on its surface, having a sample contact area for contacting a sample that contains or is suspected of containing a target tissue or cell; and
 (b) a staining solution that stains the target tissue or cell;
 wherein the first and second plates sandwich the sample and the stain solution into a thin layer of thickness that is regulated by the distance between the two sample contact areas;
 wherein the thin layer is imaged by an imager without washing the sample to remove stain solution from the sample; and
 wherein the distance between the two sample contact areas and the concentration of the stain solution in the thin layer are selected to make, during the imaging, the stained target tissue or cell in the thin layer is distinguishable from the rest of thin layer.

In some embodiments, an apparatus for analyzing the pathology of a sample without wash, comprising:
 (a) a first plate and a second plate; each, on its surface, having a sample contact area for contacting a sample that contains or is suspected of containing a target tissue or cell;
 (b) a staining solution that stains the target tissue or cell; and
 (c) an imager
 wherein the first and second plates sandwich the sample and the stain solution into a thin layer of a thickness that is regulated by the distance between the two sample contact areas;
 wherein the imager images the thin layer without washing the sample to remove stain solution from the sample; and
 wherein the distance between the two sample contact areas and the concentration of the stain solution in the thin layer are selected to make, during the imaging, the stained target tissue or cell in the thin layer is distinguishable from the rest of thin layer.

Thin layer thickness, incubation time, and background signal. According to the present invention, the thickness of the thin layer for X-Path is selected for several reasons.

(1) A thin thickness of the thin layer makes the staining solution thickness thin, which reduces the diffusion distance for a stain agent in the stain solution to across the thickness, hence reducing the diffusion time. This leads to a short incubation time and saving of the stain agent usage reducing cost.

(2) A thin thickness of the thin layer also reduce the background signal generated by the uncomsumed stain agent in the stain solution. We found experimentally that the thinner the thin layer thickness, the less the background signal, and the clearer the image of the stained cell.

Concentration of stain agent in the stain solution. According to the present invention, the concentration of the stain agent in the stain solution for X-Path is selected, so that, for a given thin layer thickness and at the end of an incubation, most of the stain agent in the stain solution is consumed for staining the target tissue or cell, having little left in the stain solution. This can reduce background signal in imaging and can save the cost on stain agent.

According to the present invention, in some embodiments of assaying (including staining) using a Q-Card, the spacer height is configured to make the assay having a stain saturation time is 5 sec, 10 sec, 20 sec, 30 sec, 60 sec, 90 sec, 120 sec, 180 sec, 300 sec, 600 sec, or a range between any two of the values. In some embodiments, the spacers have a height of 0.5 um, 1 um, 2 um, 5 um, 10 um, 20 um, 30 um, 40 um, 50 um, or a range between any two of the values.

In some preferred embodiments, the a stain saturation time is 5 sec, 10 sec, 20 sec, 30 sec, 60 sec, or a range between any two of the values. In some preferred embodiments, the spacers have a height of 0.5 um, 1 um, 2 um, 5 um, 10 um, 20 um, or a range between any two of the values. In some embodiments, the spacer is 10 um height.

FIG. 1 illustrates an embodiment of the present disclosure, in which a conformable plate comprising spacers conforms to a shape of the surface of a sample.

Figure 2:
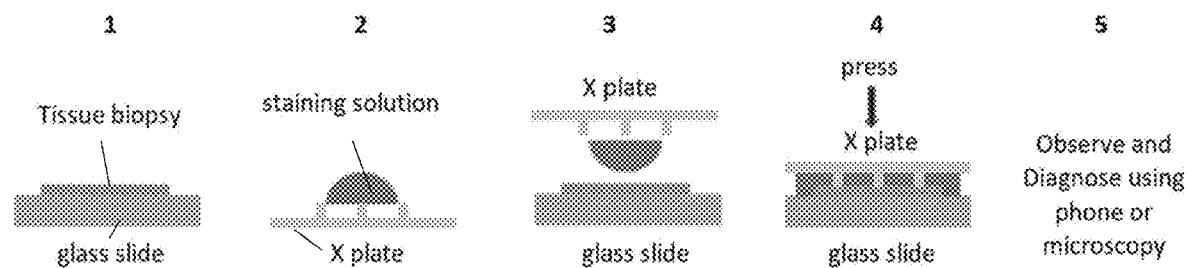
FIG. 2. Schematic figure of experimental procedure using iMOST Q-CARD microvolume embodiment. 1, place oral Q-tip brush biopsy or chicken stomach tissue biopsy (5 mm×1 mm) on sub-card or glass slide; 2, drop 10 ul (volume can be varied based on the size of tissue and pillar height) staining solution on the pillar side of X-plate; 3, place X-plate on top of glass slide with staining solution facing down towards tissues; 4, press X-plate onto tissue to allow staining solution mounting the whole piece of tissue, and to spread the tissue into micrometer thin layer (which thickness determined by pillar height); 5, leave iMOST Q-Card embodiment at room temperature for 1 min and observe under microscopy. (Note: The Term "Q-CARD" and "QMAX Card" are interchangeable.)

FIG. 2. Schematic figure of experimental procedure using iMOST Q-CARD microvolume embodiment. 1, place oral Q-tip brush biopsy or chicken stomach tissue biopsy (5 mm×1 mm) on sub-card or glass slide; 2, drop 10 ul (volume can be varied based on the size of tissue and pillar height) staining solution on the pillar side of X-plate; 3, place X-plate on top of glass slide with staining solution facing down towards tissues; 4, press X-plate onto tissue to allow staining solution mounting the whole piece of tissue, and to spread the tissue into micrometer thin layer (which thickness determined by pillar height); 5, leave iMOST Q-Card embodiment at room temperature for 1 min and observe under microscopy. (Note: The Term "Q-CARD" and "QMAX Card" are interchangeable.)

Example 1

One Step, Fast PAP Staining of Oral Mucosa Cells (OMCs)

X-Path method has been used for Papanicolaou staining (also termed "PAP staining") Papanicolaou staining solution comprising: hematoxylin, eosin azure (eosin Y, light green SF, Bismarck brown Y), orange green 6, alcohol, and water.

In the experiment, human fresh oral mucosa cells (OMCs) are used to demonstrate the one step, fast PAP staining using Q-Card. The Q-Card used has a pillar array on one of the plate as the spacer, wherein the pillars have uniform height of 10 um, and the pillar array has square lattice with a pillar size of 30 um by 40 um and a period of 110 um by 120 um.

First, the epithelial cells were taken from a subject mouth by a swap. The cells were deposited from the swap to one plate of Q-card (no spacers), forming a thin layer. Then 5-10 ul Papanicolaou staining solution was dropped on the another plate of the Q-card (X-plate having 10 um spacers), followed by pressing two plates together, which sandwich the thin epithelial cell layer and the staining solution and deform them into a uniform 10 um thick thin layer. The thin thickness of the thin layer reduces stain agent diffusion time and makes the staining reaching its saturation in less than 60 seconds, ready for imaging. Then the sample was imaged by an imaging device (e.g. laboratory microscope or smartphone based microscope).

Figure 3:
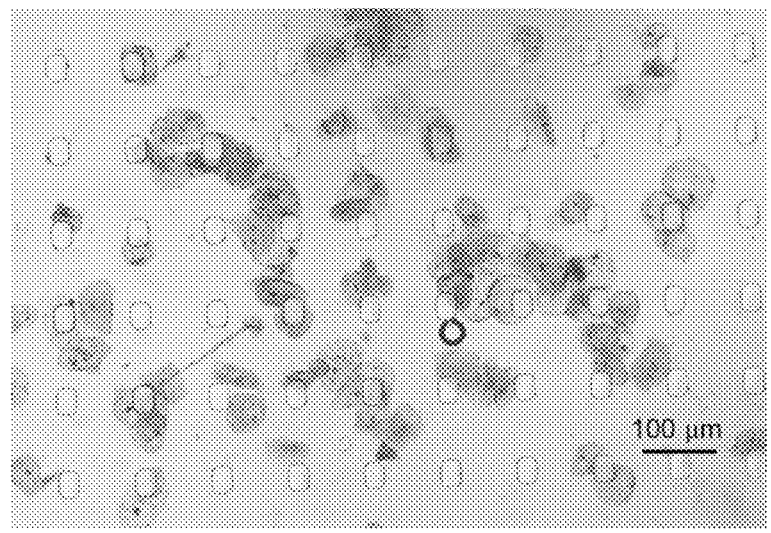
FIG. 3 Bright field microscopy image of 1 step PAP staining of oral mucosa cells (OMCs) using Q-Card. In the experiment, the Q-Card has a spacer height of 10 um with a pillar array with pillar size of 30 um by 40 um size and period of 110 um by 120 um. The OMC cells are stained to red color in the image.

FIG. 3 Bright field microscopy image of 1 step PAP staining of oral mucosa cells (OMCs) using Q-Card. In the experiment, the Q-Card has a spacer height of 10 um with a pillar array with pillar size of 30 um by 40 um size and period of 110 um by 120 um. The OMC cells are stained to red color in the image. The saturation stain incubation was leass 60 second and ready for imaging.

Another example of performing a Pap staining of OMCs using Q-Card, includes steps of:
1. Obtained a Q-Card device;
2. Used an oral swab gently collect cells from month;
3. OMC swab were first mixed with 100 to 200 ul of PBS buffer in collection tube;
4. Mixed 5 uL of OMCs PBS sample with 5 uL of PAP staining solution in collection tube for 1 min;
5. Opened the Q-Card, dropped 10 uL of mixed solution onto Q-Card, closed the Q-Card and observed using bright field imaging system, which includes microscopy and/or smartphone based microscopy system.
6. Images were analyzed using image processing software, and parameters were given to characterize each cell and nuclei, including cell size (C) and number, nuclear size (N) and number, N/C ratio, morphology, architecture distribution, nuclei segmentation and classification.

Another example of performing a Pap staining of OMCs using Q-Card, includes steps of:
1. Obtained a Q-Card device; part of pap staining solution is pre-dried on one of Q-Card plates;
2. Used an oral swab gently collect cells from month;
3. OMC swab were first mixed with buffer in collection tube;
4. Opened the Q-Card, dropped 5-10 ul of OMCs sample in collection tube onto Q-Card, wait 60 seconds, and observed using bright field imaging system, which includes microscopy and/or smartphone based microscopy system. And 5. Images were analyzed using image processing software, and parameters were given to characterize each cell and nuclei, including cell size (C) and number, nuclear size (N) and number, N/C ratio, morphology, architecture distribution, nuclei segmentation and classification.

Example 2

PAP (Papanicolaou) Staining of Cervix Swap and HPV

Pap staining using X-Path can be used for Pap tests (also termed "Pap smear"), which are tests for finding abnormal cells on patients' cervix that could lead to cervical cancer. Pap tests find cell changes caused by human papillomavirus (HPV). The present invention can make the PAP test's sample staining and preparation in a single step and in about 60 seconds, ready for imaging. The cells can be collected by a swap from a patient's cervix.

Example 3

TB Diagnostic Using Sputum

One example of the application of the present invention, is for rapid diagnosis of pulmonary tuberculosis. In some embodiments, the devices and the methods of the present invention are used for smear microscopy of sputum to detect *Mycobacterium tuberculosis* (TB) by detecting the TB cells in sputum or alike samples. The staining used in the present invention include, not limited to: 1) Ziehl-Neelsen staining, or so-called fast acid staining, to stain acids resistant mycolic acids on bacterial wall; 2) fluorescent acid fast staining using auramine-O or auramine-rhodamine, nucleic acid-binding dye SYBR® Gold.

Methodology of conventional smear microscopy detection of TB in sputum includes: 1) Ziehl-Neelsen staining, or so-called fast acid staining, to stain acids resistant mycolic acids on bacterial wall. In principle, this staining method include three major steps: staining, acid differentiation and counter-staining. Whole procedure often takes up to 1 hr with more than 10 steps. 2) fluorescent acid fast staining using auramine-O (AO) or auramine-rhodamine. The standard-AO procedure requires eight steps, three stains, and 22 min to complete (standard-AO stain kit package insert; Remel, Lenexa, KS).

The present method should shorten Ziehl-Neelsen staining and fluorescent acid fast staining procedures to 1 min as following. Ziehl-Neelsen staining (acid fast staining) of TB.

Material

1. Raw sputum or digested and decontaminated sputum;
2. Q-Card device;
3. TB staining solution include carbol fuchsin stain, acid alcohol, methylene blue and water;
4. mobile communication device or microscope.

Procedure

1. Drop 1-5 ul of digested and decontaminated sputum sample onto bottom card of Q-Card device;
2. Drop 1:1 v/v of staining solution onto X-plate of Q-Card;
3. Close Q-Card and leave at room temperature for 1 min;
4. Observe using mobile communication device or microscope.

Results: TB bacterial will show bright-red color and background tissue will show blue color on mobile communication device or microscope images. Quantification and grades of positive staining will be read and output within 1 min on mobile communication device.

I. FAST fluorescent acid fast staining of TB.

Material

1. Raw sputum or digested and decontaminated sputum;
2. Q-Card device;
3. TB staining solution include auramine rhodamine, acid alcohol, potassium permanganate and water;
4. mobile communication device or fluorescent microscope.

Procedure

1. Drop 1-5 ul of digested and decontaminated sputum sample onto bottom card of Q-Card device;
2. Drop 1:1 v/v of staining solution onto X-plate of Q-Card;
3. Close Q-Card and leave at room temperature for 1 min;
4. Observe using IPHONE or microscope.

Results: TB bacterial should show fluoresce reddish-orange against a dark background on mobile communication device or fluorescent microscope images. Non-acid-fast organisms will not fluoresce or may appear a pale yellow color on mobile communication device or fluorescent microscope images. Quantification and grades of positive staining will be read and output within 1 min on mobile communication device using software.

Another example is the Influenza Detection from Epithelial Cells using X-PATH and swap sample.

2. Rapid Tissue Sample Pre and Staining by Press Thinning

Another aspect of the present invention is a method of rapidly preparing and staining a tissue sample that has an initial thickness much thicker than the final thickness for staining and imagining analysis. Experimentally, we found that the Q-Card can press a millimeter thick fresh tissue into a film of ~10 um, and that the spacers of Q-Card can reduce or avoid damages to the cells on the tissue surface. In pressing a tissue sample by a Q-Card, the spacers prevent the top plate (i.e. the plate on the imaging size) to directly contact the tissue surface, and the top surface of a tissue sample is pressed by staining solution, which can even the pressure applied the tissue surface and avoid the "hot pot" (high pressure location) that a solid plate would create. The present invention allows a fresh tissue to be cut, load, stained and imaged in minutes and a few steps without frozen sample, without precision cutting, and without washing.

In one embodiment of the present invention, a method of rapidly preparing and staining a tissue with an initial thickness thicker than the final thickness, comprising:

(a) providing a first plate and a second plate that are movable relative to each other, wherein the second plate has spacers of uniform heights on its surface;
(b) placing, on the first plate, a tissue sample that has a thickness thicker than the spacer height;
(c) depositing a staining solution on the first plate or on the tissue, wherein the staining solution stains the tissue sample;
(d) placing the first plate on top of the tissue sample and pressing to two plates together to make the tissue sample to form a thin layer, wherein the final thickness of the tissue sample layer is less than the initial thickness of the tissue sample and is regulated by the spacers and the two plates.

After the sample preparation and staining, the sample is ready for imaging. In some embodiments, after step (c) and without washing the sample to remove stain solution from the sample, imaging the thin layer to observe the stained tissue, wherein the thickness of the thin layer and the concentration of the stain solution in the thin layer are selected to make, during the imaging, the stained target tissue or cell in the thin layer is distinguishable from the rest of thin layer.

Figure 4:
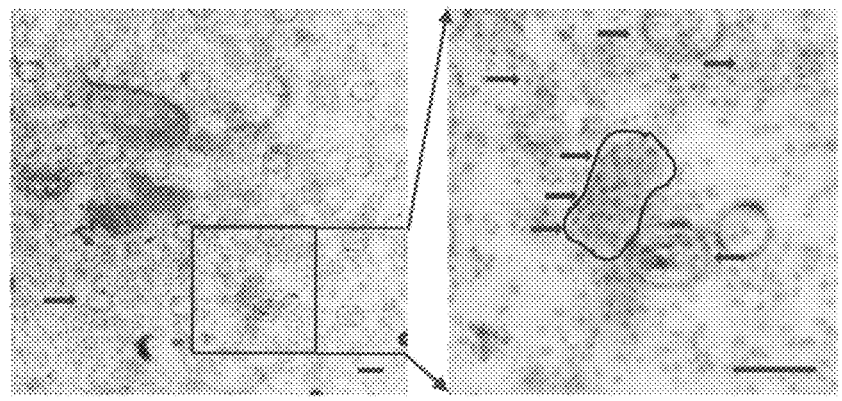
FIG. 4. Chicken stomach mucosa cytology staining by conformal press thinning with hematoxylin. Initially, a thin layer single chicken stomach (epithelial cells) tissue was ~1 mm thick. By press thinning, the tissue was significantly thinned and some location has nearly the same height as the pillar height (10 um). However, the pressed cells were not damaged. The chicken stomach epithelial cells were hematoxylin positively stained (100×, left panel) with blue/purple color (left panel). With higher magnification, the functional unit, mucosa crypt, was able to be visualized as in the green circle (right panel).

FIG. 4. Chicken stomach mucosa cytology staining by conformal press thinning with hematoxylin. Initially, a thin layer single chicken stomach (epithelial cells) tissue was ~1 mm thick. By press thinning, the tissue was significantly thinned and some location has nearly the same height as the pillar height (10 um). However, the pressed cells were not damaged. The chicken stomach epithelial cells were hematoxylin positively stained (100×, left panel) with blue/purple color (left panel). With higher magnification, the functional unit, mucosa crypt, was able to be visualized as in the green circle (right panel).

In some embodiments, the final thickness (controlled by the spacer height) of the thin layer sample is selected to make the staining time (the time that a staining reaches saturation) less 60 seconds.

In some embodiments, the time from the completion of the step (d) to imaging is 60 second or less, 120 second or less, 300 second or less, 600 second or less, 900 second or less, or a range between any two of the values.

In some embodiments, the spacers are separated from the both plates, e.g. bead or nanoparticles. In some embodiments, the beads are in the staining solution. In some embodiments, the spacers are pre-fabricated on the surface of the second plate. In some embodiments, the spacers are fabricated on the surface of the second plate and are pillar shape and have a flat top.

In some embodiments, the biopsy sample includes but not limit to exfoliated cell, exfoliated tissue, soft connective tissue, muscle tissue, liver tissue, stomach tissue, small intestine tissue, large intestine tissue, kidney tissue, heart tissue, lung tissue, bone marrow tissue, brain tissue, skin tissue, fat tissue.

In some embodiments, the biopsy sample is imprecisely cut from the biology substance. The imprecise cut means the size, thickness, and dimensions of the sample is not precisely controlled when cutting. In some embodiments, the biopsy sample is fresh without pre-processing as frozen, chemical treatments and others.

In some embodiments, the initial thickness of the tissue sample is 1 um, 5 um, 10 um, 30 um, 50 um, 100 um, 500 um 1000 um, 2000 um, 3000 um, 5000 um, or a range between any two of the values. In some embodiments, the preferred thickness of the tissue sample after cutting is 500 um, 1000 um, 2000 um, 3000 um or a range between any two of the values.

In some embodiments, the size of the tissue sample after cutting is 0.01 mm², 0.1 mm², 0.5 mm², 1 mm², 2 mm², 5 mm², 10 mm², 50 mm², 100 mm², 400 mm², 1000 mm² or a range between any two of the values. In some embodiments, the preferred size of the tissue sample after cutting is 1 mm², 2 mm², 5 mm², 10 mm², 50 mm², 100 mm², 400 mm², 1000 mm² or a range between any two of the values.

In some embodiments, the pressure of the force applied to pressing the two plates to thin the tissue sample has a pressure range of 0.1 kg/cm² to 50 kg/cm². In some embodiments, the pressure has a range of 0.5 kg/cm² to 5 kg/cm². In some embodiments, the pressure has a range of 1 kg/cm² to 3 kg/cm².

In some embodiments, the final thickness of the tissue sample after pressing is 0.1 um, 0.2 um, 0.5 um, 1 um, 5 um, 10 um, 30 um, 50 um, 100 um, 200 um, 500 um or a range between any two of the values. In some embodiments, the final thickness of the tissue sample after pressing is 1 um, 2 um, 3 um, 5 um, 10 um, or a range between any two of the values.

TABLE E1

Examples of tissue thickness change after pressing in Q-Card with 10 um pillar height

| Tissue/organ type | Initial Tissue thickness# | Final Tissue thickness |
|---|---|---|
| exfoliated cell/tissue^Δ | 0-3 mm drop or <1 mm smear | pillar height |
| soft connective tissue | 1-2 mm | pillar height |
| liver | 1-2 mm | pillar height |
| Stomach | 1-2 mm | pillar height ---~100 um |
| small intenstine | 1-2 mm | pillar height ---~100 um |
| large intestine | 1-2 mm | pillar height ---~100 um |
| kidney | 1-2 mm | pillar height ---~100 um |
| Muscle | 1-2 mm | pillar height ---~100 um |
| Heart* | 1-2 mm | pillar height ---~100 um |
| lung* | 1-2 mm | pillar height ---~100 um |
| bone marrow* | 0-3 mm drop or <1 mm smear | pillar height |
| brain* | 1-2 mm | pillar height |
| skin* | 1-2 mm | pillar height ---~100 um |
| fat* | 1-2 mm | pillar height | from scissors or blade cuts
*estimate number
^Δincluding needle and endoscopy biopsies Example of fast staining a biological surface for imaging by using one thin conformable plate and spacers. In some embodiments, only one, but two plates is used, wherein the plate is configured to conformable to the topology of a sample surface, wherein the conformable plate is configured by control the inter-spacer spacing (IDS) and increasing the plate flexibility.

The spacer height is 0.1 um, 0.2 um, 0.3 um, 0.5 um, 1 um, 2 um, 3 um, 5 um, 7 um, 10 um, or a range between any of the two values.

Examples of Biopsy Sample Thickness, Pressing Force, and Spacer Height:

In some embodiments, the biopsy sample has an original thickness of 10 um to 2000 um, the device has a spacer height of 1 um to 50 um, the pressing force is 0.5 kg/cm² to 20 kg/cm²; after pressing, the biopsy sample has an average thickness of 1 um to 100 um.

In some embodiments, the biopsy sample has an original thickness of 50 um to 1000 um, the device has a spacer height of 5 um to 30 um, the pressing force is 1 kg/cm² to 10 kg/cm²; after pressing, the biopsy sample has an average thickness of 5 um to 50 um.

In some embodiments, the biopsy sample has an original thickness of 100 um to 1000 um, the device has a spacer height of 2 to 10 um, the pressing force is 2 kg/cm² to 5 kg/cm²; after pressing, the biopsy sample has an average thickness of 2 um to 20 um.

In some embodiments, the biopsy sample has an original thickness of 500 um to 2000 um, the device has a spacer height of 2 to 30 um, the pressing force is 1 kg/cm² to 10 kg/cm²; after pressing, the biopsy sample has an average thickness of 2 um to 50 um.

In some embodiments, the biopsy sample has an original thickness of 1000 um to 2000 um, the device has a spacer height of 1 to 100 um, the pressing force is 0.5 kg/cm² to 15 kg/cm²; after pressing, the biopsy sample has an average thickness of 1 um to 150 um.

In some embodiments, the biopsy sample has an original area of 1 mm² to 100 mm², the device has a spacer height of 5 to 50 um, the pressing force is 0.5 kg/cm² to 20 kg/cm²; after pressing, the biopsy sample has an average area of 100 mm² to 1000 mm².

In some embodiments, the biopsy sample has an original area of 0.5 mm² to 10 mm², the device has a spacer height of 2 to 30 um, the pressing force is 1 kg/cm² to 10 kg/cm²; after pressing, the biopsy sample has an average area of 100 mm² to 400 mm².

The height of spacer above the biopsy sample after pressing: In some embodiments, the average height of spacer above the biopsy sample after pressing is 0.1 um, 0.2 um, 0.5 um, 1 um, 5 um, 10 um, 30 um, 50 um, or a range between any two of the values. In some embodiments, the preferred average height of spacer above the biopsy sample after pressing is 1 um, 2 um, 3 um, 5 um, 10 um, or a range between any two of the values.

The Height of Spacer Inside the Biopsy Sample after Pressing:

In some embodiments, the average height of spacer inside the biopsy sample after pressing is 0.1 um, 0.2 um, 0.5 um, 1 um, 5 um, 10 um, 30 um, 50 um, or a range between any two of the values. In some embodiments, the preferred average height of spacer inside the biopsy sample after pressing is 1 um, 2 um, 3 um, 5 um, 10 um, or a range between any two of the values.

The volume of reagent solution before pressing: In some embodiment, no liquid reagent is added into the device. In some embodiment, the staining reagent is printed onto one of the plate of the device. In some embodiment, a liquid reagent is added onto first plate, or biopsy sample or second plate before pressing. In some embodiment, the volume of liquid reagent added into the device is 0 uL, 1 uL, 2 uL, 3 uL, 5 uL, 10 uL, 20 uL, 30 uL, 50 uL or a range between any two of the values.

The thickness of the flexible plate times the Young's modulus (hE): In some embodiment, at least one of the plates is a flexible plate, and the thickness of the flexible plate times the Young's modulus of the flexible plate is in the range of 1 GPa·μm to 1000 GPa·μm.

In some embodiment, at least one of the plates is a flexible plate, and the thickness of the flexible plate times the Young's modulus of the flexible plate is in the range of 10 GPa·μm to 500 GPa·μm.

In some embodiment, at least one of the plates is a flexible plate, and the thickness of the flexible plate times the Young's modulus of the flexible plate is preferred in the range of 20 GPa·μm to 150 GPa·μm.

In some embodiment, at least one of the plates is a flexible plate, and the thickness of the flexible plate times the Young's modulus of the flexible plate is preferred in the range of 1 GPa·μm to 20 GPa·μm.

Spacer height: In some embodiment, the spacer height is 0 um, 1 um, 2 um, 3 um, 5 um, 10 um, 20 um, 30 um, 50 um, 100 um, or a range between any two of the values.

In some embodiment, the preferred spacer height is 2 um, 3 um, 5 um, 10 um, 30 um or a range between any two of the values. In some embodiment, the preferred spacer height is 2 um to 50 um. In some embodiment, the preferred spacer height is 2 um to 30 um. In some embodiment, the preferred spacer height is 5 um to 10 um. In some embodiment, the preferred spacer height is 10 um.

The fourth power of the inter-spacer-distance (ISD) divided by the thickness of the flexible plate (h) and the Young's modulus (E):

In some embodiment, a fourth power of the inter-spacer-distance (IDS) divided by the thickness (h) and the Young's modulus (E) of the flexible plate ($ISD^4/(hE)$) is $5\times10^6$ um$^3$/GPa or less.

In some embodiment, a fourth power of the inter-spacer-distance (IDS) divided by the thickness (h) and the Young's modulus (E) of the flexible plate ($ISD^4/(hE)$) is $1\times10^6$ um$^3$/GPa or less.

In some embodiment, a fourth power of the inter-spacer-distance (IDS) divided by the thickness (h) and the Young's modulus (E) of the flexible plate ($ISD^4/(hE)$) is $5\times10^5$ um$^3$/GPa or less.

The thickness of the flexible plate (h): In some embodiment, wherein the plate is a flexible plate, and the thickness of the flexible plate is 1 um to 500 um.

In some embodiment, wherein the plate is a flexible plate, and the preferred thickness of the flexible plate is 3 um to 175 um.

In some embodiment, wherein the plate is a flexible plate, and the preferred thickness of the flexible plate is 5 um to 50 um.

The Young's modulus (E): In some embodiment, at least one of the plates is a flexible plate, and the Young's modulus of the flexible plate is 0.01 GPa to 100 GPa.

In some embodiment, at least one of the plates is a flexible plate, and the Young's modulus of the flexible plate is 0.1 GPa to 50 GPa.

In some embodiment, at least one of the plates is a flexible plate, and the preferred Young's modulus of the flexible plate is 1 GPa to 5 GPa.

In some embodiment, at least one of the plates is a flexible plate, and the preferred Young's modulus of the flexible plate is 0.01 GPa to 1 GPa.

The imaging system: In some embodiment, the imaging system detect signal from sample includes but not limit to photoluminescence, electroluminescence, and electrochemiluminescence, light absorption, reflection, transmission, diffraction, scattering, or diffusion, surface Raman scattering, electrical impedance selected from resistance, capacitance, and inductance, magnetic relativity and a combination thereof.

In some embodiment, the imaging system is a microscope, a bright field microscope, phase contrast microscope, fluorescence microscope, inverted microscope, the compound light microscope, stereo microscope, digital microscope, acoustic microscope, phone based microscope.

The Analyzing System:

In some embodiment, the analyzing system includes but not limit to machine learning, supervised machine learning, unsupervised machine learning, and reinforcement learning.

In some embodiment, the analyzing system combines both the software analyzing and human analyzing.

3. Tissue Imaging Improvement Using Conformable Flexible Plate (i.e. Film) of Uniform Micro-Spacers As shown in FIG. 1, after a sample is deposited onto a substrate, a liquid is deposited onto one or both of the sample and the plate, which can comprise spacers. Upon pressing the plate together with the substrate (e.g., with the sample sandwiched therebetween), the liquid is compressed into a layer having uniform thickness, wherein the thickness of the layer is regulated by the height of the spacers. Furthermore, as the plate is flexible (e.g., conformable), the plate conforms to any irregularities in the shape of the sample, thereby maintaining a uniformly thick layer of liquid above the sample.

We found that tissue imaging improvement using conformable flexible plate (i.e. film) of uniform micro-spacers.

Example 4

Imaging Improvement

Figure 5:
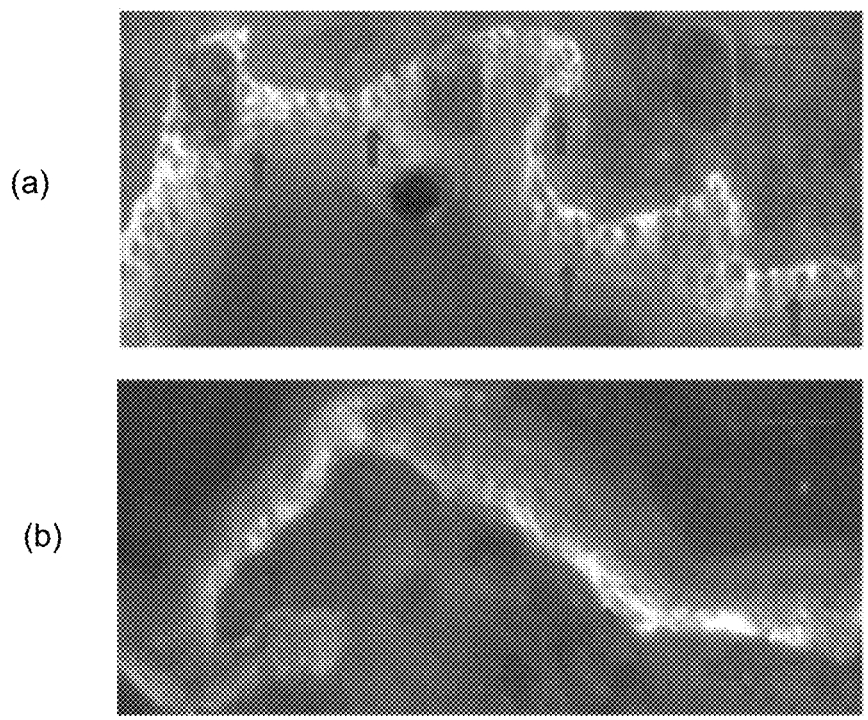
FIG. 5 illustrates a comparison between fluorescence images obtained with (i) one-step staining using an X-plate with the spacers contacting the tissue, and (ii) using flat plate. The image using X-plate have better image contrast and sharper image than that of the flat plate.

FIG. 5 illustrates a comparison between fluorescence images obtained with (i) one-step staining using an X-plate with the spacers contacting the tissue, and (ii) using flat plate. The image using X-plate have better image contrast and sharper image than that of the flat plate. Human frozen skin sections were first stained with anti-CK14-AF488 using 10 um pillar height X-plate. Tissue sections were then recovered with PBS by using X-plate (10 um pillar height, top panel) or flat PMMA film (top panel). Observe tissue sections under fluorescent microscope. Red arrows indicate CK14-AF488 positive skin epithelial cells. 10 uM pillar X-plate shows better imaging result comparing with PMMA film.

Materials. Fresh human skin and lung cryo-sections are from Zyagen, tissue sections are stored at −80° C. before use. Antibodies used in this study are all commercially prelabelled with Alexa Flour 488 (AF488). Alexa Fluor family of fluorescent dyes is a series of dyes invented by Molecular Probes, now a part of Thermo Fisher Scientific, and sold under the Invitrogen brand name. Alexa Fluor dyes are frequently used as cell and tissue labels in fluorescence microscopy and cell biology. Alexa Fluor dyes can be conjugated directly to antibodies to amplify signal and sensitivity or other biomolecules. Commercial prelabelled antibodies used in this study are anti-cytokeratin 14-AF488 (from Novus Biologicals, cat no. NBP2-34675AF488), and palloidin-AF488 (for detection of F-actin, from Thermo Fisher Scientific, cat no. A12379). All antibodies are saved at 4° C. protective from light before use. A cell membrane permeable dye acridine orange (AO, from Sigma Aldrich, cat no. A9231) is also used in the study to visualize nuclear under fluorescent microscope. X plates are manufactured in Essenlix Coop. X-Plate is 175 um thick PMMA with a pillar array of 30 um×40 um pillar size, 5 um pillar height and 80 um inter space distance.

It is one aspect of the present disclosure to provide easy and rapid devices and methods for tissue staining. In some embodiments, the reduction of the thickness of the staining liquid significantly reduces the time of staining agent(s) to diffuse across the thickness of the staining liquid, hence decreasing the saturation time for whatever purposes the staining agent(s) is for. For instance, such a configuration decreases the saturation time for antigen-antibody binding, which is the speed-limiting step of immunostaining, by reducing the diffusion distance of the antibody used for the staining, greatly promoting the overall speed for immunostaining.

It is another aspect of the present disclosure to provide uniform access to staining agent for the sample using the devices and methods for tissue staining disclosed therein. In some embodiments, the uniform thickness of the staining liquid engendered by the particular configuration of the plates and spacers ensures the uniform access of the sample to the staining agent that is dissolved and diffuses in the staining liquid.

Sample

It should be noted that, the term "sample" as used herein, unless otherwise specified, refers to a liquid bio/chemical sample or a non-liquid sample.

In some embodiments, the liquid sample is originally obtained in a liquid form, such as, blood and saliva. In some embodiments, the originally obtained sample specimen is not in a liquid state, for instance, in a solid state or a gaseous state. In such cases, the non-liquid sample is converted to a liquid form when being collected and preserved using the device and method provided by the present disclosure. The method for such conversion includes, but not limited to, mixture with a liquid medium without dissolution (the end product is a suspension), dissolution in a liquid medium, melting into a liquid form from a solid form, condensation into a liquid form from a gaseous form (e.g. exhaled breath condensate).

In some embodiments, the sample can be dried thereon at the open configuration, and wherein the sample comprises bodily fluid selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

In some embodiments, the sample contact area of one or both of the plates is configured such that the sample can be dried thereon at the open configuration, and the sample comprises blood smear and is dried on one or both plates.

In some embodiments, the sample is a solid sample, for instance, a tissue section. In some embodiments, the sample is a solid tissue section having a thickness in the range of 1-200 µm. In some embodiments, the sample contact area of one or both of the plates is adhesive to the sample. In some embodiments, the sample is paraffin-embedded. In some embodiments, the sample is fixed (e.g., formalin, paraformaldehyde and the like).

Staining Liquid

In some embodiments, the staining liquid has a viscosity in the range of 0.1 to 3.5 mPa S.

In some embodiments, one primary function of the staining liquid is to serve a transfer medium. The reagents stored (dried/coated) on the plate(s), upon contacting the staining liquid, are dissolved and diffuse in the staining liquid. As such, the staining liquid serves as a transfer medium to provide access for the reagents stored on the plate(s) to the sample.

In some embodiments, one primary function of the staining liquid is to serve as a holding solution. When the plates are pressed to enter the closed configuration, in some embodiments, the plates are configured to "self-hold" at closed configuration after the removal of the external compressing force, due to forces like capillary force provided by the liquid sample. In the cases where the sample specimen is not in a liquid form, the liquid medium therefore provides such forces like capillary force needed for the "self-holding" of the plates.

In some embodiments, the staining liquid comprises buffer pairs to balance the pH value of the final solution. In some embodiments, the staining liquid does not comprise particular component capable of altering the properties of the sample.

In some embodiments, the staining liquid comprises reagents needed for the processing, fixation, or staining of the sample, as further discussed in details in the following sections.

In some embodiments, the staining liquid comprises fixative capable of fixing the sample.

In some embodiments, the staining liquid comprises blocking agents, wherein the blocking agents are configured to disable non-specific endogenous species in the sample to react with detection agents that are used to specifically label the target analyte.

In some embodiments, the staining liquid comprises deparaffinizing agents capable of removing paraffin in the sample.

In some embodiments, the staining liquid comprises permeabilizing agents capable of permeabilizing cells in the tissue sample that contain the target analyte.

In some embodiments, the staining liquid comprises antigen retrieval agents capable of facilitating retrieval of antigen.

In some embodiments, the staining liquid comprises detection agents that specifically label the target analyte in the sample.

Plate Storage Site

In some embodiments, the sample contact area of one or both plates comprise a storage site that contains reagents needed for the processing, fixation, or staining of the sample. These reagents, upon contacting the liquid sample or the staining liquid, are dissolved and diffuse in the liquid sample/staining liquid.

In some embodiments, the sample contact area of one or both plates comprise a storage site that contains blocking agents, wherein the blocking agents are configured to disable non-specific endogenous species in the sample to react with detection agents that are used to specifically label the target analyte.

In some embodiments, the sample contact area of one or both plates comprise a storage site that contains deparaffinizing agents capable of removing paraffin in the sample. In some embodiments. the sample contact area of one or both plates comprise a storage site that contains permeabilizing agents capable of permeabilizing cells in the tissue sample that contain the target analyte.

In some embodiments. the sample contact area of one or both plates comprise a storage site that contains antigen retrieval agents capable of facilitating retrieval of antigen. In some embodiments, the sample contact area of one or both plates comprise a storage site that contains detection agents that specifically label the target analyte in the sample.

In some embodiments, the sample contact area of one or both of the plates comprise a binding site that contains capture agents, wherein the capture agents are configured to bind to the target analyte on the surface of cells in the sample and immobilize the cells.

Detection Agent

In some embodiments, the detection agent comprises dyes for a stain selected from the group consisting of: Acid fuchsin, Alcian blue 8 GX, Alizarin red S, Aniline blue WS, Auramine O, Azocarmine B, Azocarmine G, Azure A, Azure B, Azure C, Basic fuchsine, Bismarck brown Y, Brilliant cresyl blue, Brilliant green, Carmine, Chlorazol black E, Congo red, C.I. Cresyl violet, Crystal violet, Darrow red, Eosin B, Eosin Y, Erythrosin, Ethyl eosin, Ethyl green, Fast green F C F, Fluorescein Isothiocyanate, Giemsa Stain, Hematoxylin, Hematoxylin & Eosin, Indigo carmine, Janus green B, Jenner stain 1899, Light green SF, Malachite green, Martius yellow, Methyl orange, Methyl violet 2B, Methylene blue, Methylene blue, Methylene violet, (Bernthsen), Neutral red, Nigrosin, Nile blue A, Nuclear fast red, Oil Red, Orange G, Orange II, Orcein, Pararosaniline, Phloxin B, Protargol S, Pyronine B, Pyronine, Resazurin, Rose Bengal, Safranine O, Sudan black B, Sudan III, Sudan IV, Tetrachrome stain (MacNeal), Thionine, Toluidine blue, Weigert, Wright stain, and any combination thereof.

In some embodiments, the detection agent comprises antibodies configured to specifically bind to protein analyte in the sample.

In some embodiments, the detection agent comprises oligonucleotide probes configured to specifically bind to DNA and/or RNA in the sample.

In some embodiments, the detection agent is labeled with a reporter molecule, wherein the reporter molecule is configured to provide a detectable signal to be read and analyzed.

In some embodiments, the reporter molecule comprises fluorescent molecules (fluorophores), including, but not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, redshifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5',5"-dibromopyrogallol sulfonaphthalein (Bromopyrogallol Red); 7-diethylamino-3-(4'-isothiocyanato-phenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)amino-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; ophthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of 5 sulforhodamine (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl)aminonaphthalene-1-sulfonic acid (EDANS), 4-(4'-dimethylaminophenylazo) benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from Aequoria victoria or a derivative thereof, e.g., a "humanized" derivative such as Enhanced GFP; a GFP from another species such as *Renilla reniformis, Renilla mulleri,* or *Ptilosarcus* guernyi; "humanized" recombinant GFP (hrGFP); any of a variety of fluorescent and colored proteins from Anthozoan species; any combination thereof; and the like.

In some embodiments, the signal is selected from the group consisting of:
  i. luminescence selected from photo-luminescence, electroluminescence, and electrochemiluminescence;
  ii. light absorption, reflection, transmission, diffraction, scattering, or diffusion;
  iii. surface Raman scattering;
  iv. electrical impedance selected from resistance, capacitance, and inductance;
  v. magnetic relaxivity; and
  vi. any combination of i-v.

Immunohistochemistry

In some embodiments, the devices and methods of the present disclosure are useful for conducting immunohistochemistry on the sample.

In immunohistochemical (IHC) staining methods, a tissue sample is fixed (e.g., in paraformaldehyde), optionally embedding in wax, sliced into thin sections that are less then 100 µm thick (e.g., 2 µm to 6 µm thick), and then mounted onto a support such as a glass slide. Once mounted, the tissue sections may be dehydrated using alcohol washes of increasing concentrations and cleared using a detergent such as xylene. In certain cases, fixation is also an optional step, for instance, for blood smear staining.

In most IHC methods, a primary and a secondary antibody may be used. In such methods, the primary antibody binds to antigen of interest (e.g., a biomarker) and is unlabeled. The secondary antibody binds to the primary antibody and directly conjugated either to a reporter molecule or to a linker molecule (e.g., biotin) that can recruit reporter molecule that is in solution. Alternatively, the primary antibody itself may be directly conjugated either to a reporter molecule or to a linker molecule (e.g., biotin) that can recruit reporter molecule that is in solution. Reporter molecules include fluorophores (e.g., FITC, TRITC, AMCA, fluorescein and rhodamine) and enzymes such as alkaline phosphatase (AP) and horseradish peroxidase (HRP), for which there are a variety of fluorogenic, chromogenic and chemiluminescent substrates such as DAB or BCIP/NBT.

In direct methods, the tissue section is incubated with a labeled primary antibody (e.g. an FITC-conjugated antibody) in binding buffer. The primary antibody binds directly with the antigen in the tissue section and, after the tissue section has been washed to remove any unbound primary antibody, the section is to be analyzed by microscopy.

In indirect methods, the tissue section is incubated with an unlabeled primary antibody that binds to the target antigen in the tissue. After the tissue section is washed to remove unbound primary antibody, the tissue section is incubated with a labeled secondary antibody that binds to the primary antibody.

After immunohistochemical staining of the antigen, the tissue sample may be stained with another dye, e.g., hematoxylin, Hoechst stain and DAPI, to provide contrast and/or identify other features.

The present device may be used for immunohistochemical (IHC) staining a tissue sample. In these embodiments, the device may comprise a first plate and a second plate, wherein: the plates are movable relative to each other into different configurations; one or both plates are flexible; each of the plates has, on its respective surface, a sample contact area for contacting a tissue sample or a IHC staining liquid; the sample contact area in the first plate is smooth and planner; the sample contact area in the second plate comprise spacers that are fixed on the surface and have a predetermined substantially uniform height and a predetermined constant inter-spacer distance that is in the range of 7 µm to 200 µm;

wherein one of the configurations is an open configuration, in which: the two plates are completely or partially separated apart, the spacing between the plates is not regulated by the spacers; and wherein another of the configurations is a closed configuration which is configured after a deposition of the sample and the IHC staining liquid in the open configuration; and in the closed configuration: at least part of the sample is between the two plates and a layer of at least part of staining liquid is between the at least part of the sample and the second plate, wherein the thickness of the at least part of staining liquid layer is regulated by the plates, the sample, and the spacers, and has an average distance between the sample surface and the second plate surface is equal or less than 250 µm with a small variation.

As discussed above, in some embodiments, the device may comprise a dry IHC staining agent coated on the sample contact area of one or both plates. In some embodiments, the device may comprise a dry IHC staining agent coated on the sample contact area of the second plate, and the IHC staining liquid comprise a liquid that dissolve the dry IHC staining agent. In some embodiments, the thickness of the sample is 2 µm to 6 µm.

H&E, Special Stains, and Cell Viability Stains

In some embodiments, the devices and methods of the present disclosure are useful for conducting H&E stain, special stains, and cell viability stains.

Hematoxylin and eosin stain or haematoxylin and eosin stain (H&E stain or HE stain) is one of the principal stains in histology. It is the most widely used stain in medical diagnosis and is often the gold standard; for example when a pathologist looks at a biopsy of a suspected cancer, the histological section is likely to be stained with H&E and termed "H&E section", "H+E section", or "HE section". A combination of hematoxylin and eosin, it produces blues, violets, and reds.

In diagnostic pathology, the "special stain" terminology is most commonly used in the clinical environment, and simply means any technique other than the H&E method that is used to impart colors to a specimen. This also includes immunohistochemical and in situ hybridization stains. On the other hand, the H&E stain is the most popular staining method in histology and medical diagnosis laboratories.

In any embodiments, the dry binding site may comprise a capture agent such as an antibody or nucleic acid. In some embodiments, the releasable dry reagent may be a labeled reagent such as a fluorescently-labeled reagent, e.g., a fluorescently-labeled antibody or a cell stain such Romanowsky's stain, Leishman stain, May-Grunwald stain, Giemsa stain, Jenner's stain, Wright's stain, or any combination of the same (e.g., Wright-Giemsa stain). Such a stain may comprise eosin Y or eosin B with methylene blue. In certain embodiments, the stain may be an alkaline stain such as haematoxylin.

In some embodiments, the special stains include, but not limited to, Acid fuchsin, Alcian blue 8 GX, Alizarin red S, Aniline blue WS, Auramine O, Azocarmine B, Azocarmine G, Azure A, Azure B, Azure C, Basic fuchsine, Bismarck brown Y, Brilliant cresyl blue, Brilliant green, Carmine, Chlorazol black E, Congo red, C.I. Cresyl violet, Crystal violet, Darrow red, Eosin B, Eosin Y, Erythrosin, Ethyl eosin, Ethyl green, Fast green F C F, Fluorescein Isothiocyanate, Giemsa Stain, Hematoxylin, Hematoxylin & Eosin, Indigo carmine, Janus green B, Jenner stain 1899, Light green SF, Malachite green, Martius yellow, Methyl orange, Methyl violet 2B, Methylene blue, Methylene blue, Methylene violet, (Bernthsen), Neutral red, Nigrosin, Nile blue A, Nuclear fast red, Oil Red, Orange G, Orange II, Orcein, Pararosaniline, Phloxin B, Protargol S, Pyronine B, Pyronine, Resazurin, Rose Bengal, Safranine O, Sudan black B, Sudan III, Sudan IV, Tetrachrome stain (MacNeal), Thionine, Toluidine blue, Weigert, Wright stain, and any combination thereof.

The term "cell viability stains" refers to staining technology used to differentially stain live cells and dead cells inside a tissue sample. Usually the difference in cell membrane and/or nucleus membrane permeability between live and dead cells are taken advantage for the differential staining. In other cases, markers for apoptosis or necrosis (indicating dying cells or cell corpses) are used for such staining.

In some embodiments, the device comprises, on one or both of the plates, a dye to stain the sample for cell viability. In some embodiments, the dye includes, but not limited to, Propidium Iodide (PI), 7-AAD (7-Aminoactinomycin D), Trypan blue, Calcein Violet AM, Calcein AM, Fixable Viability Dye (FVD) conjugated with different fluorophores, SYTO9 and other nucleic acid dyes, Resazurin and Formazan (MTT/XTT) and other mitochondrial dyes, and any combination thereof and the like. In some embodiments, the sample comprises bacteria, and it is desirable to determine the bacterial viability in the sample, the device further comprises, on one or both of the plates, a bacterial viability dye, for instance, PI, SYTO9, and the like, to differentially stain the live cells versus dead cells. Optionally, the device further comprises, on one or both of the plates, dyes for total bacterial staining, for instance, gram staining reagents and the like.

In Situ Hybridization

In some embodiments, the devices and methods of the present disclosure are useful for conducting in situ hybridization (ISH) on histological samples.

In situ hybridization (ISH) is a type of hybridization that uses a labeled complementary DNA, RNA or modified nucleic acids strand (i.e., probe) to localize a specific DNA or RNA sequence in a portion or section of tissue (in situ), or, if the tissue is small enough (e.g., plant seeds, Drosophila embryos), in the entire tissue (whole mount ISH), in cells, and in circulating tumor cells (CTCs).

In situ hybridization is used to reveal the location of specific nucleic acid sequences on chromosomes or in tissues, a crucial step for understanding the organization, regulation, and function of genes. The key techniques currently in use include: in situ hybridization to mRNA with oligonucleotide and RNA probes (both radio-labelled and hapten-labelled); analysis with light and electron microscopes; whole mount in situ hybridization; double detection of RNAs and RNA plus protein; and fluorescent in situ hybridization to detect chromosomal sequences. DNA ISH can be used to determine the structure of chromosomes. Fluorescent DNA ISH (FISH) can, for example, be used in medical diagnostics to assess chromosomal integrity. RNA ISH (RNA in situ hybridization) is used to measure and localize RNAs (mRNAs, lncRNAs, and miRNAs) within tissue sections, cells, whole mounts, and circulating tumor cells (CTCs).

In some embodiments, the detection agent comprises nucleic acid probes for in situ hybridization staining. The nucleic acid probes include, but not limited to, oligonucleotide probes configured to specifically bind to DNA and/or RNA in the sample.

Systems and Methods for Tissue Staining and Cell Imaging

Also provided is a system for rapidly staining and analyzing a tissue sample using a mobile phone, comprising:
    (a) sample, staining liquid, and device as described above,
    (b) a mobile communication device comprising:
        i. one or more cameras for detecting and/or imaging the sample;
        ii. electronics, signal processors, hardware and software for receiving and/or processing the detected signal and/or the image of the sample and for remote communication; and
    (c) a light source from either the mobile communication device or an external source.

Also provided is a method for rapidly staining and analyzing a tissue sample using a mobile phone, comprising:
    (a) depositing a tissue sample and a staining liquid on the device of the system described above, and placing the two plate into a closed configuration;
    (b) obtaining a mobile phone that has hardware and software of imaging, data processing, and communication;
    (c) assaying by the tissue sample deposited on the CROF device by the mobile phone to generate a result; and
    (d) communicating the result from the mobile phone to a location remote from the mobile phone.

4. Rapid Homogenous Intracellular Assay

Most of the assays today (except pathology and cytology) detect a biomarker related to a disease or disorder in bio system by detecting the biomarker in a sample while the biomarker is outside a cell (e.g. the biomarker leaks out from a cell into a sample or a cell in a sample is lysed). Often the concentration of biomarker outside a cell may be low that makes a detection of the biomarker challenging and/or complicated.

One aspect of the present invention is to detect a biomarker while the biomarker is still inside a cell. One reason for such approach is that the concentration of a biomarker in a cell is generally much higher than that when the biomarker comes out the cell into the sample. For example, for a biomarker originally in lymphocyte, the concentration of the biomarker in lymphocyte can be ~5,000 times higher than that if the lymphocyte is lysed and the biomarker is mixed in the blood. Such high biomarker concentration cell can greatly facilitate the biomarker detection.

Figure 6:
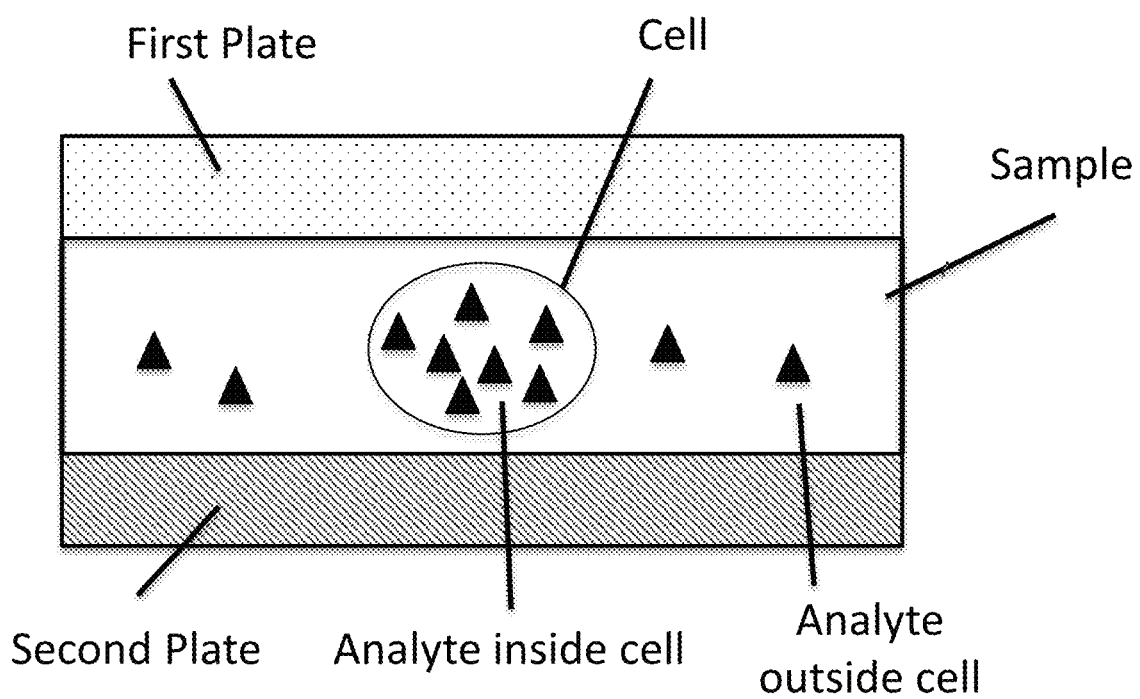
FIG. 6. Illustration of intra-cellular assay. A sample with a cell sandwiched between two plates, wherein the cell contains analytes (i.e. biomarkers) inside of the cell, and some of analytes are outside the cell. In some embodiments, the analyte concentration inside the cell has a colleration with that outside the cell.

FIG. 6. Illustration of intra-cellular assay. A sample with a cell sandwiched between two plates, wherein the cell contains analytes (i.e. biomarkers) inside of the cell, and some of analytes are outside the cell. In some embodiments, the analyte concentration inside the cell has a colleration with that outside the cell.

One aspect of the present invention is to detect a biomarker in a cell for detecting a disease or disorder in a bio system, by introducing a labeled probe into a cell, wherein the labeled probe specifically bines to the biomarker.

One aspect of the present invention, the labeled probe comprises protein, nucleic acids, aptamer, or a combination thereof.

AA. In some embodiment, a method for a rapid homogenous detection of an analyte inside a membrane of a cell in a sample, comprising:
    (a) providing a first plate and a second plate, each, on its surface, having a sample contact area for contacting a sample comprising a cell that contains or is suspected of containing an analyte inside the cell,
    (b) providing a detection probe that (i) specifically binds the analyte and (ii) is capable of emitting a light at a wavelength;
    (c) providing a permeabilization reagent that makes a membrane of the cell permeable to the detection probe, wherein without the permeabilization reagent the detection probe cannot permeate into the cell;
    (d) sandwiching the sample, the detection probe, and the permeabilization reagent between the first and second plates to form a thin layer of a thickness of 200 microns (um) or less; and
    (e) after the step (d) and without washing the sample to remove unbound detection probe, imaging the thin layer to detect the cell that has the analyte bound to the detection probe;
    wherein the thickness of the thin layer and the concentration of the detection probe in the thin layer are selected to make, in the thin layer, the signal from the location having the detection probe bound to the analyte inside the cell distinguishable from signals from the locations that do not have the cell during the imaging of step (e).

The method of embodiment AA, the imaging of step (e) is performed 300 seconds or less after sandwiching of step (d).

The method of embodiment AA, wherein the thickness of the thin layer is selected to make some of the cell having no overlap or significant overlap with other cells in the thin layer.

The method of embodiment AA, further comprising a step of quantifying (i) the cell that has an analyte inside the cell and (ii) the cell that does have an analyte inside the cell.

The method of embodimentAA, further comprising a step of quantifying (i) the cell that has an analyte inside the cell and (ii) the cell that does have an analyte inside the cell, and a step of quantifying the percentage of the cell having an analyte inside the cell relative to the total number of the cell.

The method of embodimentAA, wherein the light emitted by the detection probe is fluorescence, and wherein the method further comprises (i) measuring the fluorescence intensity of the cell having the analyte bound to the detection probe, (ii) measuring the number of the cells having the analyte bound to the detection probe, and (iii) calculating a total fluorescence intensity by multiplying the total number of cells having the analyte bound to the detection probe in a unit area and the average of the fluorescence intensity of the cell having the analyte bound to the detection probe.

Example 25 Viral Detection

According to the present invention, a method of a detection of a viral infection of a subject comprising: detecting a virus specific glycoprotein inside a cell of the subject (i.e. glycoprotein inside a membrane of a cell), wherein a virus glycoprotein specific probe is introduced inside a cell (e.g. inside plasma and/or nucleus), wherein the probe has a label, wherein the probe concentration in the cell is configured so that at least one portion of the volume of the cell has a concentration of the probes bound to a specific virus glycol-protein higher than that of unbind probes in a portion of the volume of (i) other portion of the cell and/or (ii) other portion of a volume outside of the cell. In some embodiments, the staining reagent may comprise a permeabilizing agent capable of permeabilizing cells in the tissue sample that contain the target analyte.

In some embodiments, the analyte is glycol-protein of the viras.

In some embodiments, the spacers are separated from the both plates, e.g. bead or nanoparticles. In some embodiments, the beads are in the staining solution. In some embodiments, the spacers are pre-fabricated on the surface of the second plate. In some embodiments, the spacers are fabricated on the surface of the second plate and are pillar shape and have a flat top.

In some embodiments, staining solution include: PH7 to PH8 buffer for antibody staining, such as PBS, Saline, Tris buffer, HEPES buffer, sodium bicarbonate.

In some embodiments, staining solution include detergent such as: 1-6% Zwittgent In some embodiments, a permearization of cell is by:
i. Organic solvent based solutions: 50%-70% ethanol or isopropyl alcohol in buffer;
ii. Nanoparticle carriers to deliver antibody into white blood cells, such as lipid or polymetric based nanoparticles;
iii. Electroporation to deliver antibody into white blood cells;
iv. Peptide mediated antibody delivery into white blood cells; or
v. any combination of above.

Example of FAST staining and imaging of virus in white blood cells from whole blood patent material.
Sample Collection:
1. Massage to warm the finger and increase blood flow by gently squeezing from hand to fingertip 5-6 times. Wipe dry with clean gauze or allow to air dry.
2. Using a sterile lancet, make a skin puncture just off the center of the finger pad.
3. Wipe away the first drop of blood. Finger smear 1-5 ul of second drop of whole blood directly onto Q-Card.

Staining and Imaging:
1. Mix blood with staining solution including PBS, Zwittgent, ethanol and fluorophore labelled antibody.
2. Close Q-Card and incubate blood sample with staining solution at room temperature for less than 1 min without any washing;
3. After 2, Image white blood cells in the closed Q-Card using iPHONE or fluorescent microscope.

Exemplary embodiments of Q-Card, pillar size 0.1-2 um, 2-10 um, 10-30 um.

Exemplary embodiments of Imaging devices: iPHONE or fluorescent microscope

Exemplary embodiments in Staining and Imaging:
Exemplary embodiments in Sampling: any biological samples containing virus:
a. blood specimens
b. respiratory specimens
c. cutaneous specimens
d. cervical specimens
e. stool specimens
f. urine specimens
g. Cerebrospinal fluid specimens
h. Any other fine needle specimens, such as amniotic fluid Examples of Virus can be detected by the present invention include, not limited to:
a. CMV, hepatitis B virus, hepatitis C, EBV and HIV in blood specimen
b. HSV and VZV in cutaneous specimens
c. Rotavirus in stool specimens
d. RSV, influenza and Parainfluenza viruses, and Adenovirus in respiratory specimens
e. HPV in cervical and cutaneous specimens
f. HSV in Cerebrospinal fluid specimens
g. Zika virus in amniotic fluid specimens Biomarks and Applications Further aspects of the present disclosure include a CROF device that includes a plurality of capture agents that each binds to a plurality of analytes in a sample, i.e., a multiplexed CROF device. In such instances, the CROF device containing a plurality of capture agents can be configured to detect different types of analytes (protein, nucleic acids, antibodies, etc.). The different analytes can be distinguishable from each other on the array based on the location within the array, the emission wavelength of the detectable label that binds to the different analytes, or a combination of the above.

Other pathogens that can be detected in a diagnostic sample using the devices, systems and methods in the present invention include, but are not limited to: *Varicella zoster Staphylococcus epidermidis, Escherichia coli*, methicillin-resistant *Staphylococcus aureus* (MSRA), *Staphylococcus aureus, Staphylococcus hominis, Enterococcus faecalis, Pseudomonas aeruginosa, Staphylococcus capitis, Staphylococcus wameri, Klebsiella pneumoniae, Haemophilus influenzae, Staphylococcus simulans, Streptococcus pneumoniae* and *Candida albicans*; gonorrhea (*Neisseria gorrhoeae*), syphilis (*Treponena pallidum*), clamydia (*Clamyda tracomitis*), nongonococcal urethritis (*Ureaplasm urealyticum*), chancroid (*Haemophilus ducreyi*), trichomoniasis (*Trichomonas vaginalis*); *Pseudomonas aeruginosa*, methicillin-resistant *Staphlococccus aureus* (MSRA), *Klebsiella pneumoniae, Haemophilis influenzae, Staphylococcus aureus, Stenotrophomonas maltophilia, Haemophilis parainfluenzae, Escherichia coli, Enterococcus faecalis, Serratia marcescens, Haemophilus parahaemolyticus,*

*Enterococcus cloacae, Candida albicans, Moraxiella catarrhalis, Streptococcus pneumoniae, Citrobacter freundii, Enterococcus faecium, Klebsella oxytoca, Pseudomonas fluorscens, Neiseria meningitidis, Streptococcus pyogenes, Pneumocystis carinii, Klebsella pneumoniae Legionella pneumophila, Mycoplasma pneumoniae,* and *Mycobacterium tuberculosis*, etc., as well as those listed in Tables B2 and 6.

Below is a list of diseases and the Diagnostic Markers associated with them:

Alzheimer's disease: Aβ42, amyloid beta-protein (CSF), prion protein (CSF), proapoptotic kinase R (PKR) and its phosphorylated PKR (pPKR) (CSF)

multiple sclerosis: fetuin-A (CSF), niemann-pick type C: tau (CSF), bipolar disorder: secretogranin II (CSF), prion disease: prion protein (CSF)

HIV-associated neurocognitive disorders: Cytokines (CSF)

Parkinsonian disorders (neuordegenerative disorders): Alpha-synuclein (CSF), tau protein (CSF), Apo H (CSF), ceruloplasmin (CSF), Peroxisome proliferator-activated receptor gamma coactivator-1 alpha (PGC-1α)(CSF)

axonal degeneration: neurofilament light chain (CSF)

neurodegenerative disorders: parkin (CSF), PTEN induced putative kinase 1 (CSF), DJ-1 (CSF), leucine-rich repeat kinase 2 (CSF)

Kufor-Rakeb disease: mutated ATP13A2 (CSF)

CSF rhinorrhea (nasal surgery samples): transthyretin (CSF)

Multiple Sclerosis Progression: Vitamin D-binding Protein (CSF), CXCL13 (CSF)

intrathecal inflammation: IL-12p40, CXCL13 and IL-8 (CSF)

prostate cancer: Dkk-3 (semen)

Sepsis (Endocan, specifically secreted by activated-pulmonary vascular endothelial cells, is thought to play a key role in the control of the lung inflammatory reaction): p14 endocan fragment (blood)

neuromyelitis optica: Serum (blood)

cardiovascular disease: ACE2 (blood), alpha-amylase (saliva)

early diagnosis of esophageal squamous cell carcinoma: autoantibody to CD25 (blood)

lung cancer: hTERT (blood), CAI25 (MUC 16) (blood): VEGF (blood), sIL-2 (blood), Osteopontin (blood), BRAF, CCNI, EGRF, FGF19, FRS2, GREB1, and LZTS1 (saliva)

ovarian cancer: Human epididymis protein 4 (HE4) (blood), CA 125 (saliva)

pregnancy: Alpha-Fetal Protein (blood)

diabetics: Albumin (urine)

albuminuria: albumin (urine) uria kidney leaks: microalbuminuria mirror fetal AFP levels: AFP (urine)

Acute kidney injury: neutrophil gelatinase-associated lipocalin (NGAL) (urine), interleukin 18 (IL-18) (urine), Kidney Injury Molecule-1 (KIM-1) (urine), Liver Fatty Acid Binding Protein (L-FABP) (urine)

Epstein-Barr virus oncoprotein (nasopharyngeal carcinomas): LMP1 (saliva), BARF1 (saliva)

oral cancer: IL-8 (saliva)

oral or salivary malignant tumors: carcinoembryonic antigen (CEA) (saliva)

Malignant tumors of the oral cavity: carcinoembryonic antigen (saliva)

spinalcellular carcinoma: IL8 (saliva), thioredoxin (saliva)

HIV: beta-2 microglobulin levels—monitor activity of the virus (saliva), tumor necrosis factor-alpha receptors—monitor activity of the virus (saliva)

breast cancer: CA15-3 (saliva)

In some instances, the present method is used to inform the subject from whom the sample is derived about a health condition thereof. Health conditions that may be diagnosed or measured by the present method, device and system include, but are not limited to: chemical balance; nutritional health; exercise; fatigue; sleep; stress; prediabetes; allergies; aging; exposure to environmental toxins, pesticides, herbicides, synthetic hormone analogs; pregnancy; menopause; and andropause. The following Table B3 provides a list of biomarker that can be detected using the present invention, and their associated health conditions.

Oral squamous Cell Carcinoma: p53

Head and neck squamous cell carcinoma: CASP-8, SART-1, TREX1, 3' repair exonuclease; BRAP (BRCA1 associated): Nuclear localization protein; Trim 26 zinc finger domains; GTF21 transcription factor. Murine homolog TF11-1; NSEP1 (YB-1) transcription factor; MAZ transcription factor associated with c-myc; SON (DBP-5; KIAA1019; NREBP DNA binding protein); NACA nascent polypeptide-associated complex; NUBP2 nucleotide binding protein; EEF2 Translation elongation factor 2; GU2 Putative RNA helicase; RPLI3A ribosomal protein; SFRS21P (CASP11; SIP1; SRRP1290 splicing factor); RPS12 ribosomal protein; MGC2835 RNA helicase; TMF1, TATA modulatory factor; PRC1 regulator of cytokinesis; KRT14 keratin 14; Viniculin; H2AFY histone family member; SLK (KIAA02304) Ste related kinase; NOL3 (ARC) nuclear protein 3, apoptosis repressor; DNAJA2 member of Hsp40 family; DNAJA1 member of HSP40 family; LINE-1 retrotransposon; MOG (HSPC 165) Homolog of yeast protein; LIMS1 (PINCH): LIM and senescent antigen-like domain; COPB2 coatomer protein complex subunit protein; FLJ22548 hypothetical protein; C21orf97; FLJ21324; MGC15873; SSNA1 Sjogrens syndrome nuclear autoantigen 1; KIAA0530, zinc finger domain; rat stannin; hypothetical protein DKFZp4340032; human FLJ23089; PC326

1. Anionic Detergent

Alkyl Sulfates: Lithium dodecyl sulfate, Lithium dodecyl sulfate, Lithium dodecyl sulfate, Niaproof®, Sodium 2-ethylhexyl sulfate, Sodium dodecyl sulfate, Sodium octyl sulfate, Teepol™ 610 S anionic, Turkey red oil sodium salt Alkyl Sulfonates: 1-Octanesulfonic acid sodium salt, 4-Dodecylbenzenesulfonic acid, Ethanesulfonic acid sodium salt, Sodium 1-butanesulfonate, Sodium 1-decanesulfonate, Sodium 1-heptanesulfonate, Sodium 1-nonanesulfonate, Sodium 1-octanesulfonate, Sodium 1-pentanesulfonate, Sodium 1-propanesulfonate, Sodium hexanesulfonate, Sodium pentanesulfonate Bile Salts: Chenodeoxycholic acid diacetate methyl ester, Chenodeoxycholic acid, Cholic acid, Deoxycholic acid, Glycocholic acid hydrate, Sodium chenodeoxycholate, Sodium cholate hydrate, Sodium cholate hydrate, Sodium cholate hydrate, Sodium cholesteryl sulfate, Sodium deoxycholate, Sodium glycochenodeoxycholate, Sodium glycocholate, Sodium glycodeoxycholate, Sodium taurochenodeoxycholate, Sodium taurocholate, Sodium taurodeoxycholate, Sodium taurohyodeoxycholate, Sodium taurolithocholate, Sodium tauroursodeoxycholate, Taurocholic acid sodium salt, Taurolithocholic acid 3-sulfate disodium salt, Ursodeoxycholic acid Other Anionic Detergents: Dicyclohexyl sulfosuccinate sodium salt, Dihexadecyl phosphate, Dihexyl sulfosuccinate sodium salt, Docusate sodium, Lithium 3,5-diiodosalicylate, N-Lauroylsarcosine sodium salt, N-Lauroylsarcosine, N-Lauroylsarcosine purum, Sodium octanoate, Triton™ QS-15

2. Cationic Detergents

Alkyltrimethylammonium bromide, Amprolium hydrochloride, Benzalkonium chloride, Benzethonium hydroxide, Benzyldimethyldodecylammonium, Benzyldimethylhexadecylammonium, Benzyldodecyldimethylammonium, Cetylpyridinium chloride, Dimethyldioctadecylammonium, Dodecylethyldimethylammonium, Dodecyltrimethylammonium, Ethylhexadecyldimethylammonium bromide, Girard's reagent T, Hexadecyl(2-hydroxyethyl)dimethylammonium dihydrogen phosphate, Hexadecylpyridinium bromide, Hexadecylpyridinium chloride, Hexadecyltrimethylammonium, Luviquat™ FC 370, Luviquat™ FC 550, Luviquat™ HOLD, Luviquat™ Mono LS, Methylbenzethonium chloride, Myristyltrimethylammonium, Tetraheptylammonium bromide, Tetrakis(decyl)ammonium bromide, Tri-C8-10-alkylmethylammonium chloride, Tridodecylmethylammonium chloride Selectophore™

3. Non-Ionic Detergent

1-Oleoyl-rac-glycerol, 2-Cyclohexylethyl β-D-maltoside, 4-Nonylphenyl-polyethylene glycol non-ionic, 5-Cyclohexylpentyl β-D-maltoside, 6-Cyclohexylhexyl β-D-maltoside, n-Dodecanoylsucrose, n-Dodecyl-β-D-glucopyranoside, n-Dodecyl-β-D-maltoside, n-Nonyl-β-D-glucopyranoside, n-Octyl-β-D-thioglucopyranoside, n-Decanoylsucrose, n-Decyl-β-D-maltopyranoside, n-Octanoylsucrose, n-Octyl-β-D-glucopyranoside, APO-10, APO-12, BRIJ® O20, BRIJ® 35, Big CHAP, Deoxy, Brij® 58, Brij® L23, Brij® L4, Brij® O10, Cremophor EL®, $C_{12}E_8$, $C_{12}E_9$, DGEA, Decaethylene glycol mono-dodecyl ether nonionic surfactant, Decyl β-D-glucopyranoside, Decyl β-D-maltopyranoside, Decyl-β-D-1-thiomaltopyranoside, Decyl-β-D-maltoside, Diethylene glycol, Digitonin, Digitoxigenin, ELUGENT™ Detergent, Ethylene glycol, GC Stationary Phase phase Synperonic PE/F68, GC Stationary Phase phase Synperonic PE/L64, GENAPOL® X-100, Genapol® C-100, Genapol® X-080, Genapol® X-100, Glucopone 600 CS UP, HECAMEG®, Hexaethylene glycol monododecyl ether, Hexaethylene glycol monohexadecyl ether, Hexaethylene glycol monotetradecyl ether, Hexyl β-D-glucopyranoside, IGEPAL® CA-630, IGEPAL® CA-720, IPTG, Imbentin AGS/35, Isopropyl β-D-1-thiogalactopyranoside, Kolliphor® EL, Lutrol® OP 2000 non-ionic, Methoxypolyethylene glycol 350, Methyl 6-O—(N-heptylcarbamoyl)-α-D-glucopyranoside, N,N-Bis[3-(D-gluconamido)propyl] deoxycholamide, N,N-Dimethyldecylamine N-oxide, N,N-Dimethyldodecylamine N-oxide, N-Decanoyl-N-methylglucamine, N-Lauroyl-L-alanine, N-Nonanoyl-N-methylglucamine, N-Octanoyl-N-methylglucamine, NP-40 Alternative, Nonaethylene glycol monododecyl ether nonionic surfactant, Nonidet™ P 40, Nonyl β-D-glucopyranoside, Nonyl β-D-maltoside, Nonyl-β-D-1-thiomaltoside, Nonylphenyl-polyethyleneglycol acetate, Octaethylene glycol monodecyl ether, Octaethylene glycol monododecyl ether, Octaethylene glycol monohexadecyl ether, Octyl β-D-1-thioglucopyranoside, Octyl β-D-glucopyranoside, Octyl-α/β-glucoside, Octyl-β-D-glucopyranoside, PLURONIC® F-127, Pentaethylene glycol monodecyl ether, Pluronic® F-127, Poloxamer 188, Poloxamer 407, Poly(ethylene glycol) methyl ether, Polyoxyethylene (10) tridecyl ether mixture of C11 to C14 iso-alkyl ethers, Polyoxyethylene (20) sorbitan monolaurate, Polyoxyethylene (40) stearate, Polysorbate 20, Polysorbate 60, Polysorbate 80, SODOSIL™ RM 003, SODOSIL™ RM 01, diethylene glycol octadecyl ether, Saponin, Span® 20, Span® 60, Span® 65, Span® 80, Span® 85, Sucrose monodecanoate, Sucrose monolaurate, Synperonic® F 108, Synperonic® PE P105, TERGITOL™ TMN 10, TERGITOL™ TMN 6, TERGITOL™ solution Type NP-40, TERGITOL™ MIN FOAM, TERGITOL™ Type 15-S-5, TERGITOL™ Type 15-S-7, TERGITOL™ Type 15-S-9, TERGITOL™ Type NP-10, TERGITOL™ Type NP-9, TRITON® X-100, TRITON® X-114, TWEEN® 20, TWEEN® 40, TWEEN® 60, TWEEN® 65, TWEEN® 80, TWEEN® 85, Tetradecyl-β-D-maltoside, Tetraethylene glycol monododecyl ether, Tetraglycol, Tetramethylammonium hydroxide pentahydrate, Thesit®, Tridecyl β-D-maltoside, Triethylene glycol monodecyl ether, Triton™ N-57, Triton™ N-60, Triton™ X-100, Triton™ X-102, Triton™ X-114, Triton™ X-165, Triton™ X-305, Triton™ X-405, Triton™ X-45, Tween® 20, Tween® 40, Tween® 60, Tween® 80, Tween® 85, Tyloxapol, Undecyl β-D-maltoside, n-Dodecyl β-D-glucopyranoside, n-Dodecyl β-D-maltoside, n-Heptyl β-D-glucopyranoside, n-Heptyl β-D-thioglucopyranoside, n-Hexadecyl β-D-maltoside, n-Octyl β-D-maltoside 4. Zwitterionic (Ampholytic)

3-(4-tert-Butyl-1-pyridinio)-1-propanesulfonate, 3-(N,N-Dimethylmyristylammonio)propanesulfonate, 3-(N,N-Dimethyloctadecylammonio)propanesulfonate, 3-(N,N-Dimethyloctylammonio)propanesulfonate, 3-(N,N-Dimethylpalmitylammonio)propanesulfonate, 3-(1-Pyridinio)-1-propanesulfonate, 3-(Benzyldimethylammonio)propanesulfonate, 3-(Decyldimethylammonio)-propane-sulfonate inner salt, 3-[N,N-Dimethyl(3-palmitoylaminopropyl)ammonio]-propanesulfonate, L-α-Lysophosphatidylcholine from Glycine max (soybean), ASB-14, zwitterionic amidosulfobetaine. ASB-16 zwitterionic amidosulfobetaine detergent, ASB-C80, ASB-C8Ø, C7BzO, CHAPS, CHAPSO, DDMAB, Dimethylethylammoniumpropane, EMPIGEN® BB Detergent, Miltefosine, N-Dodecyl-N,N-dimethyl-3-ammonio-1-propanesulfonate, N-Dodecyl-N,N-dimethyl-3-ammonio-1-propanesulfonate, O-(Decylphosphoryl)choline, Poly(maleic anhydride-alt-1-decene), 3-(dimethylamino)-1-propylamine derivative, Poly(maleic anhydride-alt-1-tetradecene), 3-(dimethylamino)-1-propylamine derivative, Sodium 2,3-dimercaptopropanesulfonate, Surfactin from *Bacillus subtilis*, ZWITTERGENT® 3-08, ZWITTERGENT® 3-10, ZWITTERGENT® 3-12, ZWITTERGENT® 3-14, ZWITTERGENT® 3-16, Below is a list of organic solvent can be used to permeabilize cell membrane:

Hydrocarbons: n-Pentane, n-Hexane, n-Heptane, n-Octane, n-Nonane, n-Decane, 2,2,4-Trimethyl pentane, Cyclohexane, Benzene, Toluene, Ethyl benzene, Xylene (mixed isomers), C9 Aromatics, Tetralin Alcohols: Methano, I Ethano, I n-Propanol, i-Propanol, n-Butanol, i-Butanol, s-Butanol, n-Amyl alcohol, i-Amyl alcohol, Cyclohexanol, n-Octanol, Ethanediol, Diethylene glycol, 1,2-Propanediol Glycol ethers: Propylene glycol methyl ether, Ethylene glycol methyl ether, Ethylene glycol ethyl ether, Ethylene glycol monobutyl ether Chlorinated solvents: Methylene chloride, Chloroform, Carbon tetrachloride, 1,2-Dichloroethane, 1,1,1-Trichloroethane, Trichloroethylene, Perchloroethylene, Monochlorobenzen Ketones: Acetone, Methyl ethyl ketone, Methyl isobutyl ketone, Cyclohexanone, n-Methyl-2-pyrrolidone, Acetophenone Ethers: Diethyl ether, Diisopropyl ether, Dibutyl ether, Methyl tert butyl ether, 1,4-Dioxane, Tetrahydrofuran Esters: Methyl acetate, Ethyl acetate, Isopropyl acetate, n-Butyl acetate, Cellosolve acetate Miscellaneous solvents: Dimethylformamide, Dimethylacetamide, Dimethylsulphoxide, Sulfolane, Carbon disulphide, Acetic acid, Aniline, Nitrobenzene, Morpholine, Pyridine, 2-Nitropropane, Acetonitrile, Furfuraldehyde, Phenol, Water Nanoparticles for Intracellular Delivery
1. Inorganic Nanomaterials: gold, silver, calcium phosphate, graphene oxide, quantum dots, and magnetic nanomaterials such as iron oxides. Graphene oxide
2. Carbon Nanotubes (CNTs): multiwalled carbon nanotubes (MWNTs), single walled carbon nanotubes (SWNTs), Polyethylenimine(PEI)-MWNTs, PEI-cholesterol-MWNTs, Succinated PEI (PEI-SA)-CNTs, chitosan-folic acid nanoparticles (CS-FA NPs), functionalized carboxylated MWNTs (fCNT),
3. Proteins and Peptide Nanomaterials
4. Polymer-Based Nanomaterials
5. Lipid-based nanomaterials, see liposomes
6. Liposomes Various Lipids and Amphiphiles that are Used as Liposome Raw Materials

| | |
|---|---|
| Natural phospholipids | Phosphotidylcholine, Phosphotidylserine, Phosphotidylethanolamine |
| Synthetic phospholipids | 1,2-Dilauroyl-sn-Glycero-3-Phosphocoline (DLPC), 1,2-Dioleoyl-sn-Glycero-3-[Phospho-L-Serine] (Sodium Salt) (DOPS), Dipalmitoylphosphotidylcholine, Dipalmitoylphosphotidylseine, Distearoylphosphotidylcholine, Dipalmitoylphosphotidylglycerol, 1,2-Dilauroyl-sn-Glycero-3-Phosphocholine (DLPC) |
| Unsaturated | 1-Stearoyl-2-Linoleoyl-sn-Glycero-3-[Phospho-L-Serine] (Sodium Salt), Dioleaylphosphotidylcholine |
| Sphingolipids | Shingomyellin |
| Glycosphingolipids | Gangliosides |
| Steroids | Cholesterol |
| Polymeric material | Lipids conjugated to diene, methacrylate & thiol group |
| Charge-inducing lipids | Diotadecyldimethyl ammonium bromide/chloride (DODAB/C); Dioleoyl trimethylammonium propane (DOTAP) |

Types of Liposomes:
Liposomes, Archaeosomes, Niosomes, Novasomes, Cryptosomes, Emulsomes, Vesosomes
7. Polyethyleneglycol (PEG)
8. Polyethyleneimine (PEI)
9. Natural Polymer-Based Nanomaterials E. Examples of Applications of Present Invention in Diagnosis of Diseases and Disorders E-1. Diagnosis of Diseases Associated with Infectious Diseases, Including Bacterial, Viral, Fungal, and Parasitic Infections The devices and the methods in the present invention can be used for diagnosing diseases, including *Acinetobacter baumannii*, *Acinetobacter* infections, *Actinomyces gerencseriae*, *Actinomyces israelii*, Actinomycosis, Aids, alphaviruses, Amebiasis, Amoebic dysentery, *Anabaena*, anaemia, *Anaplasma* genus, Anaplasmosis, mold spores including Aspergillius *flavis*, anthrax, Anthrax, *Aphanizomenon*, *Arcanobacterium haemolyticum* infection, Arenaviruses, Argentine hemorrhagic fever, Arsenicosis, ascariasis, Ascariasis, *Ascaris lumbricoides*, Aspergillius *glaucus*, Aspergillius *niger*, *Aspergillosis*, *Aspergillus* genus, Astroviridae family Babesiosis, Astrovirus infection, avian influenza, *Bacillus anthracis*, *Bacillus magaterium* sp. (Veg), *Bacillus magaterium* sp. (Spores), *Bacillus paratyphusus*, *Bacillus subtilis*, Bacterial vaginosis (BV), Bacteriophage (*E. coli*), Bacteroides infection, blue-green algae, Bolivian hemorrhagic fever, Botulinum Toxin, Botulism, Brazilian hemorrhagic fever, *Brucella*, brucellosis, bubonic pague, Bunyaviridae family, *Burkholderia mallei*, *Burkholderia pseudomallei*, Buruli ulcer *Mycobacterium*, Caliciviridae family, Campylobacteriosis, Candidiasis (Moniliasis; Thrush), castor beans, chagas disease, *Chlamydia*, *Chlamydia psittaci*, *Chlamydophila* pneumonia, *Chlamydophila pneumoniae* infection, Cholera, *Clostridium botulinum*, *Clostridium difficile* infection, *Clostridium perfringens*, *Clostridium tetani* (Tetanus/Lockjaw), coliform bacteria, *Coxiella burnetii*, Crimean-Congo haemorrhagic fever, *Cryptosporidium*, *Cryptosporidium* parvun, cyanobacterial toxins, Cylindroapermopsis raciborski, Cylindrospermopis, Dengue, diphtheria, *E. coli* O157:H7, *E. coli*, eastern equine encephalitis, Eberthella typosa, Ebola virus, *Entamoeba histolytica*, Epsilon toxin, *Escherichia coli* O157:H7, Fluorosis, Francisella tularensis, Giardia Lamblia, Glanders, gonorrhea, Guanarito virus, H1N1, H5N1, hantavirus, Hendra Virus, Hepatitis, Hepatitis A Virus, Hepatitis B Virus, Hepatitis C Virus, Hepatitis D Virus, Hepatitis E Virus, Herpes simplex virus 1 and 2 (HSV-1 and HSV-2), HIV, hookworm disease otitis media, human monkeypox, Influenza (Flu), Japanese Encephaltis, junin virus, Lassa fever, Lassa virus, legionellosis, leishmaniasis, Lenionella, leprosy, *Leptospira* Canicoal-infections (Jaundice), Leptospirosis, lymphatic filariasis, Machupo virus, Malaria, Marburg haemorrhagic fever, Marburg virus, measles, Melioidosis, meningitis, meningococcal disease, Methaemoglobinemia, Methicillin-resistant *Staphylococcus Aureus* (MRSA) *Micrococcus candidus*, *Micrococcus* spheroids, microcystin, *Mucor racemosus* A, *Mucor racemosus* B, *Mycobacterium tuberculosis* (Tuberculosis), *Neisseria catarrhalis*, Nipah virus, *Nodularia*, *Nostoc*, Onchocerciasis, *Oospora lactis*, *Oscillatoria*, Paratyphoid enteric fevers, *Penicillium digitatum*, *Penicillium expansum*, *Penicillium roqueforti*, pertussis, Phtomomnas aeruginosa, plague, poliomyelitis, Poliovirus-Poliomyelitis, *Propionibacterium propionicus*, *Pseudomonas fluorescens*, Psittacosis, Q fever, respiratory infections, Rhisophus *nigricans*, Ricin toxin, *Ricinus communis*, *Rickettsia prowazekii*, rift valley fever, Ringworm, Rotovirus, Sabia, *Salmonella* enteritidis, *Salmonella* paratyphi (Enteic Fever), *Salmonella* species, *Salmonella Typhi*, *Salmonella typhimurium*, *Salmonella* typhosa (Typhoid Fever), salmonellosis, *Sarcina lutea*, Scabie, Schistomsomiasis, schistosomiasis, *Serratia marcescens*, *Shigella*, *Shigella dysenteriae* (Dysentery), *Shigella flexneri*-(Dysentery), *Shigella* paradysenteriae, Shigellosis, Smallpox,

*Spirillum rubrum*, staphylococcal enterotoxin B, *Staphylococcus albus* (Staph), *Staphylococcus aureus* (Staph), *Streptococcus* hemolyticus, *Streptococcus lactis, Streptococcus* viridians, swine influenza, syphilis, *Tinea*, Tobacco *mosaic, Trachoma*, trichuriasis, trypanosomiasis, tuberculosis, Tularemia, Typhoid fever, typhus fever, ulcerans Calicivirus infection (Norovirus and Sapovirus), Umezaka, *Variola major*, Venezuelan equine encephalitis, Venezuelan hemorrhagic fever, *Vibrio* cholera, viral encephalitis, Viral hemorrhagic fevers, yellow fever, *Yersinia pestis*, and *Yersinia pestis*.

E-2. Diagnosis of Cancers

The devices and the methods in the present invention can be used for diagnosing cancers which include but not limit to:

Acute Lymphoblastic Leukemia (ALL), Acute Myeloid Leukemia (AML), Adolescents, Adrenocortical Carcinoma, Childhood Adrenocortical Carcinoma, AIDS-Related Cancers, Kaposi Sarcoma (Soft Tissue Sarcoma), AIDS-Related Lymphoma (Lymphoma), Primary CNS Lymphoma (Lymphoma), Anal Cancer, Gastrointestinal Carcinoid Tumors, Astrocytomas, Childhood (Brain Cancer), Atypical Teratoid/Rhabdoid Tumor, Childhood, Central Nervous System (Brain Cancer);

Basal Cell Carcinoma of the Skin—Skin Cancer, Bile Duct Cancer, Bladder Cancer, Childhood Bladder Cancer, Bone Cancer (includes Ewing Sarcoma and Osteosarcoma and Malignant Fibrous Histiocytoma), Brain Tumors, Breast Cancer, Childhood Breast Cancer, Bronchial Tumors, Childhood, Burkitt Lymphoma—Non-Hodgkin Lymphoma;

Carcinoid Tumor (Gastrointestinal), Childhood Carcinoid Tumors, Carcinoma of Unknown Primary, Childhood Carcinoma of Unknown Primary, Cardiac (Heart) Tumors, Central Nervous System tumors, Atypical Teratoid/Rhabdoid Tumor, Childhood (Brain Cancer), Embryonal Tumors, Childhood (Brain Cancer), Germ Cell Tumor, Childhood (Brain Cancer), Primary CNS Lymphoma, Cervical Cancer, Childhood Cervical Cancer, Childhood Cancers, Cancers of Childhood, Unusual, Cholangiocarcinoma—Bile Duct Cancer, Chordoma, Childhood—Unusual Cancers of Childhood, Chronic Lymphocytic Leukemia (CLL), Chronic Myelogenous Leukemia (CML), Chronic Myeloproliferative Neoplasms, Colorectal Cancer, Childhood Colorectal Cancer, Craniopharyngioma, Childhood (Brain Cancer), Cutaneous T-Cell Lymphoma—Lymphoma (Mycosis Fungoides and Sézary Syndrome);

Ductal Carcinoma In Situ (DCIS)—Breast Cancer,

Embryonal Tumors, Central Nervous System, Childhood (Brain Cancer), Endometrial Cancer (Uterine Cancer), Ependymoma, Childhood (Brain Cancer), Esophageal Cancer, Childhood Esophageal Cancer; Esthesioneuroblastoma (Head and Neck Cancer); Ewing Sarcoma (Bone Cancer); Extracranial Germ Cell Tumor, Childhood; Extragonadal Germ Cell Tumor; Eye Cancer; Childhood Intraocular Melanoma; Intraocular Melanoma; Retinoblastoma;

Fallopian Tube Cancer; Fibrous Histiocytoma of Bone, Malignant, and Osteosarcoma;

Gallbladder Cancer; Gastric (Stomach) Cancer; Childhood Gastric (Stomach) Cancer; Gastrointestinal Carcinoid Tumor; Gastrointestinal Stromal Tumors (GIST) (Soft Tissue Sarcoma); Childhood Gastrointestinal Stromal Tumors; Germ Cell Tumors; Childhood Central Nervous System Germ Cell Tumors (Brain Cancer); Childhood Extracranial Germ Cell Tumors; Extragonadal Germ Cell Tumors; Ovarian Germ Cell Tumors; Testicular Cancer; Gestational Trophoblastic Disease;

Hairy Cell Leukemia; Head and Neck Cancer; Heart Tumors, Childhood; Hepatocellular (Liver) Cancer; Histiocytosis, Langerhans Cell; Hodgkin Lymphoma; Hypopharyngeal Cancer (Head and Neck Cancer);

Intraocular Melanoma; Childhood Intraocular Melanoma; Islet Cell Tumors, Pancreatic Neuroendocrine Tumors; Kaposi Sarcoma (Soft Tissue Sarcoma); Kidney (Renal Cell) Cancer; Langerhans Cell Histiocytosis; Laryngeal Cancer (Head and Neck Cancer); Leukemia; Lip and Oral Cavity Cancer (Head and Neck Cancer); Liver Cancer; Lung Cancer (Non-Small Cell and Small Cell); Childhood Lung Cancer; Lymphoma;

Male Breast Cancer; Malignant Fibrous Histiocytoma of Bone and Osteosarcoma; Melanoma; Childhood Melanoma; Melanoma, Intraocular (Eye); Childhood Intraocular Melanoma; Merkel Cell Carcinoma (Skin Cancer); Mesothelioma, Malignant; Childhood Mesothelioma; Metastatic Cancer; Metastatic Squamous Neck Cancer with Occult Primary (Head and Neck Cancer); Midline Tract Carcinoma With NUT Gene Changes; Mouth Cancer (Head and Neck Cancer); Multiple Endocrine Neoplasia Syndromes; Multiple Myeloma/Plasma Cell Neoplasms; Mycosis Fungoides (Lymphoma); Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms, Chronic;

Nasal Cavity and Paranasal Sinus Cancer (Head and Neck Cancer); Nasopharyngeal Cancer (Head and Neck Cancer); Neuroblastoma; Non-Hodgkin Lymphoma; Non-Small Cell Lung Cancer;

Oral Cancer, Lip and Oral Cavity Cancer and Oropharyngeal Cancer (Head and Neck Cancer); Osteosarcoma and Malignant Fibrous Histiocytoma of Bone; Ovarian Cancer; Childhood Ovarian Cancer; Pancreatic Cancer; Childhood Pancreatic Cancer; Pancreatic Neuroendocrine Tumors (Islet Cell Tumors); Papillomatosis (Childhood Laryngeal); Paraganglioma; Childhood Paraganglioma; Paranasal Sinus and Nasal Cavity Cancer (Head and Neck Cancer); Parathyroid Cancer; Penile Cancer; Pharyngeal Cancer (Head and Neck Cancer); Pheochromocytoma; Childhood Pheochromocytoma; Pituitary Tumor; Plasma Cell Neoplasm/Multiple Myeloma; Pleuropulmonary Blastoma; Pregnancy and Breast Cancer; Primary Central Nervous System (CNS) Lymphoma; Primary Peritoneal Cancer; Prostate Cancer;

Rectal Cancer; Recurrent Cancer; Renal Cell (Kidney) Cancer; Retinoblastoma; Rhabdomyosarcoma, Childhood (Soft Tissue Sarcoma); Salivary Gland Cancer (Head and Neck Cancer); Sarcoma; Childhood Rhabdomyosarcoma (Soft Tissue Sarcoma); Childhood Vascular Tumors (Soft Tissue Sarcoma); Ewing Sarcoma (Bone Cancer); Kaposi Sarcoma (Soft Tissue Sarcoma); Osteosarcoma (Bone Cancer); Soft Tissue Sarcoma; Uterine Sarcoma; Sézary Syndrome (Lymphoma); Skin Cancer; Childhood Skin Cancer; Small Cell Lung Cancer; Small Intestine Cancer; Soft Tissue Sarcoma; Squamous Cell Carcinoma of the Skin; Squamous Neck Cancer with Occult Primary, Metastatic (Head and Neck Cancer); Stomach (Gastric) Cancer; Childhood Stomach (Gastric) Cancer;

T-Cell Lymphoma, Cutaneous—Lymphoma (Mycosis Fungoides and Sezary Syndrome); Testicular Cancer; Childhood Testicular Cancer; Throat Cancer (Head and Neck Cancer); Nasopharyngeal Cancer; Oropharyngeal Cancer; Hypopharyngeal Cancer; Thymoma and Thymic Carcinoma; Thyroid Cancer; Transitional Cell Cancer of the Renal Pelvis and Ureter (Kidney (Renal Cell) Cancer); Unknown Primary, Carcinoma of; Childhood Cancer of Unknown Primary; Unusual Cancers of Childhood; Ureter and Renal Pelvis, Transitional Cell Cancer (Kidney (Renal Cell) Cancer; Urethral Cancer; Uterine Cancer, Endometrial; Uterine Sarcoma; Vaginal Cancer; Childhood Vaginal Cancer; Vascular Tumors (Soft Tissue Sarcoma); Vulvar Cancer; Wilms Tumor and Other Childhood Kidney Tumors.

One aspect of the present disclosure is to provide devices and methods for easy and rapid tissue staining by utilizing a pair of plates that are movable to each other to manipulate a tissue sample and/or a small volume of staining liquid, reducing sample/staining liquid thickness, making a contact between the sample and staining reagent, etc. —all of them have beneficial effects on the tissue staining (simplify and speed up stain, wash free, and save reagent)

Another aspect of the present disclosure is to provide for easy and rapid tissue staining by coating staining reagents on one or both of the plate(s), which upon contacting the liquid sample and/or the staining liquid, are dissolved and diffuse in the sample and/or the staining liquid, easing the handling of staining reagents with no need of professional training.

Another aspect of the present disclosure is to ensure uniform access of the sample to the staining reagent by utilizing the plates and a plurality of spacers of a uniform height to force the sample and/or staining liquid to form a thin film of uniform thickness, leading to same diffusion distance for the staining reagents across a large lateral area over the sample.

Another aspect of the present disclosure is to provide systems for easy and rapid tissue staining and imaging by combining the pair of plates for staining with a mobile communication device adapted for acquiring and analyzing images of the tissue sample stained by the plates. Optionally, the mobile communication is configured to send the imaging data and/or analysis results to a remote location for storage and/or further analysis and interpretation by professional staff or software.

Another aspect of the present disclosure is to provide devices, systems and methods for immunohistochemistry.

Another aspect of the present disclosure is to provide devices, systems and methods for H&E stains, special stains, and/or cell viability stains.

Another aspect of the present disclosure is to provide devices, systems and methods for in situ hybridization.

Another aspect of the present disclosure is to provide devices, systems and methods for staining biological materials (e.g. for staining of cells or tissues, nucleic acid stains, H&E stains, special stains, and/or cell viability stains. etc.) without washing, and in some embodiments, in a single step.

Using CROF Cards in Cytology/Cytopathology Screening and Diagnosis

Some embodiments of the present invention are related to collect and analyze a sample using cytology quickly and simply.

According to the present invention, a method of collecting and analyzing a sample using cytology comprising:
  having a first plate and a second plate that are movable relative to each other;
  collecting a biological sample (i.e. biopsy) from a subject (e.g. a human or animal);
  depositing a part of the sample on an inner surface of a first plate;
  depositing a staining solution on either (i) surface of the first plate and/or on top of the sample, (ii) inner surface of the second plate, or (iii) both,
  bringing the two plate together to a closed configuration, in which, the two inner surfaces of the first and second plates are facing each other and the spacing between the plates is regulated by spacers between the plate, and at least a part of the staining solution is between the sample and the inner surface of the second plate;
  having an imager; and
  imaging the sample for analysis.

In some embodiments, the analysis by imaging is cytoanalysis.

In some embodiments, the spacers are fixed on one or both plates. In some embodiments, the spacers are inside of the staining solution.

In some embodiments, the sample is mixed with the staining solution before dropped on the plate.

In some embodiments, the staining solution comprises staining agent (things that stain cells/tissue) in a solution. In some embodiments, the staining solution does not comprises staining dye in a solution, but is configured to transport a staining agent coated on one of the plates into the cells/tissue. In some embodiments, the staining solution comprises staining agent (things that stain cells/tissue) in a solution, and is configured to transport a staining agent coated on one of the plates into the cells/tissue.

In some embodiments, the spacer height is configured to make the stained cells and/or tissues be visible by an imaging device without washing away the staining solution between the second plate and the sample.

In some embodiments, the spacer height is configured to make the stained cells and/or tissues be visible by an imaging device without open the plates after the plates reached a closed configuration.

In some embodiments, a sample was stained without washing away the staining solution between the second plate and the sample, and imaged by an imager, after closing the plates into a closed configuration, and without washing, imaged by an imager.

In some embodiments, a sample was stained without washing away the staining solution between the second plate and the sample, and imaged by an imager, after closing the plates into a closed configuration, in 30 seconds or less, 60 seconds or less, 120 seconds or less, 300 seconds or less, 600 seconds or less, or a range between any of the two.

In some preferred embodiments, a sample was stained without washing away the staining solution between the second plate and the sample, and imaged by an imager, after closing the plates into a closed configuration, in 30 seconds or less, 60 seconds or less, 120 seconds or less, or a range between any of the two.

In some preferred embodiments, a sample was stained without washing away the staining solution between the second plate and the sample, and imaged by an imager, after closing the plates into a closed configuration, in 30 seconds or less, 60 seconds or less, or a range between any of the two.

In some embodiments, the spacer height is 0.2 um (micron) or less, 0.5 um or less, 1 um or less, 3 um or less, 5 um or less, 10 um or less, 20 um or less, 30 um or less, 40 um or less, 50 um or less, or a range between any of the two.

In some preferred embodiments, the spacer height is 3 um or less. In some preferred embodiments, 10 um or less. In some preferred embodiments, 20 um or less. In some preferred embodiments, 30 um or less.

In some preferred embodiments, the staining solution has, after the plates are in a closed configuration, a thickness that is equal or less than sub-noise thickness.

The term "sub-noise thickness" (SNT) reference to the a thickness of a sample or a staining solution, which is thinner than a thickness where the noise in the sample or in the staining solution is below the signal from a specifically bound optical label, making the optical label visible to an imager. Making a staining solution less than the SNT will remove the need to wash away the unbind optical labels.

In some embodiments, the first plate and the second plate are connected by a hinge.

In some embodiments, the staining solution has a volume 2 uL (micro-liter) or less, 2 uL or less, 5 uL or less, 10 uL or less, 15 uL or less, 20 uL or less, 30 uL or less, 50 uL or less, 100 uL or less, or a range between any of the two.

In some preferred embodiments, the staining solution has a volume 2 uL (micro-liter) or less, 2 uL or less, 5 uL or less, 10 uL or less, 15 uL or less, 20 uL or less, 30 uL or less, or a range between any of the two.

In some preferred embodiments, the staining solution has a volume 2 uL (micro-liter) or less, 2 uL or less, 5 uL or less, 10 uL or less, 15 uL or less, or a range between any of the two.

Example of oral cancer diagnostics. According to the present invention, the sample is epithelial cells that exfoliated by a swab from the mouth of a subject. An oral cancer diagnostics can be done by measuring the size and/or area of an epithelial cell and its nucleus, and/or by measuring the ratio of the size and/or of them. For example, a cancer epithelial cell typically has a ratio of the areas (and/or size) of the nucleus to the area larger than that a norm epithelial cell.

Example of screen smoker from non-smoker. According to the present invention, the sample is epithelial cells that exfoliated by a swab from the mouth of a subject. An oral cancer diagnostics can be done by measuring the size and/or area of an epithelial cell and its nucleus, and/or by measuring the ratio of the size and/or of them. A smoker has an epithelial cell that typically has, compared with a non-smoker, a different ratio of the areas (and/or size) of the nucleus to the area larger than that a norm epithelial cell.

One application of the present invention is in cytopathology. Cytopathology is commonly used to investigate disease at cellular level using free cells or tissue fragments removed from a wide range of body sites. It has been the main tool utilized to screen and diagnose cancer and some infectious diseases or other inflammatory conditions. For example, a common application of cytopathology is the Pap smear, a screening tool used to detect precancerous cervical lesions that may lead to cervical cancer.

Some examples of the present invention in cytology/cytopathology are diagnosis based on haematoxylin and eosin (H&E) stained slides to the current regular evaluation of tumors by immunocytochemistry (ICC) and in situ hybridization (ISH) to confirm tumor histogenesis, subtype, and to provide additional information influencing prognosis and treatment in cancers.

In some embodiments, several ways are used to remove biopsy from a subject's body sites: needle, endoscopy and excisional or incisional surgery.

One aspect of the present invention is the devices and methods for performing a biopsy processing and staining in simple way. Different from standard cytopathology of preparing sample, sampling on slide, followed by staining biopsy on slide, exemplary embodiments advantage the three steps into one single step, in detail, place drop, slice, or block of biopsy material directly onto underneath card holder which can be conventional glass slide, a micrometer height chamber, or any type of holder. Place X-plate pillar side down and gently press X-plate together with staining solution onto biopsy samples. Pressing X-plate onto sample is able to spread bulk of sample into monolayer which thickness prefixed by pillar height (10 um). with two main features: 1) predefined micrometer (5 um, 10 um or higher) height pillar on X-plate for evenly processing/spreading biopsy samples into single cell based monolayer without changing cell's or tissue's morphology; 2) predefined microvolume chamber significantly fast staining time to less than 1 min.

Using microvolume embodiment for cytopathology 1) sample processing and 2) staining.

For example, in certain embodiments, the QMAX device is used to process (press) biopsy material to monolayer. Biopsy material can be collected from:

Sample Taking Methods. In some embodiments, a biopsy sample is removed by using one or a combination of the following methods: needle aspiration, endoscopy and excisional or incisional surgery.

needle biopsy from skin lesion, lymph node, thyroid, mammary gland, lung and body cavity tissue Smear from oral brush material, cervical (pap smear), body fluid: urine, sputum (phlegm), spinal fluid, pleural fluid, pericardial fluid, ascitic fluid.

endoscopy biopsy from

GI tract: esophagus, stomach, and duodenum (esophagogastroduodenoscopy), small intestine (enteroscopy), large intestine/colon (colonoscopy, sigmoidoscopy), bile duct, rectum (rectoscopy), and anus (anoscopy);

respiratory tract: nose (rhinoscopy), lower respiratory tract (fiberoptic bronchoscopy)

Ear: otoscopy urinary tract: cystoscopy female reproductive tract (gynoscopy): cervix (colposcopy), uterus (hysteroscopy), fallopian tubes (falloposcopy).

through a small incision: abdominal or pelvic cavity (laparoscopy), interior of a joint (arthroscopy), organs of the chest (thoracoscopy and mediastinoscopy).

Surgery biopsy from any excisionally or incisionally removed tissue or mass

In certain embodiments, the QMAX device is used to stain any molecular, organelle, cellular, outer cellular or organoid structure.

biological molecule include, but not limited to: protein, peptide, amino acids (selenocysteine, pyrrolysine, carnitine, ornithine, GABA and taurine), lipid (glycolipids, phospholipids, sterols, arachidonic acid, prostaglandins, leukotrienes), fatty acids, carbohydrates (monosaccharides, disaccharides, polysaccharides), nucleic acids (nucleotide, oligonucleotide, polynucleotides), any catabolites, any metabolites, secondary metabolites, vitamins, reactive oxygen/nitrogen species, minerals, polyphenolic macromolecule, and other small molecules, etc.

modification/reaction of biological molecules include, but not limited to: phosphorylation, methylation, acetylation, lipidation, thiol reactions, amine reaction, carboxylate reactions, hydroxyl reactions, aldehyde and ketone reactions, etc.

cellular organelle/subcellular structure include, but not limited to: nucleus, ribosome, peroxisomes, endoplasmic reticulum, golgi apparatus, mitochondria, lysosome, cell membrane, endosome, exosome, cytoskeleton.

type of cells with any physiological/pathological conditions include, but not limited to: within a tumor (can be originated from any epithelial from any organ, and vessel endothelial cells, fibroblast, lymphocyte), neuronal cells, lipocytes, stromal cells, chondrocytes, retinal cells, glial cells, smooth muscle cells, any type of stem cells, any type of embryonic cells, any type of endocrine cells, any type of exocrine cells, any type of immune cells, dendritic cells, myeloid cells, hematopoietic cells, lymphocyte, normal cells, benign cells, premalignant cells, malignant cells, transformation cells, quiescent cells, proliferation cells, apoptotic cells, senescent cells, mitotic cells, inflammatory cells, hyperplasia cells, hypertrophy cells, atrophy cells, hyperplasia cells, dysplasia cells, metaplasia cells etc.

connective tissue/extracellular structures include, but not limited to: Loose ordinary connective tissue, adipose tissue, blood and blood forming tissues, dense ordinary connective tissue, cartilage, bone, any type of extracellular vesicles, extracellular matrix, platelet, etc.

In some embodiments, the materials and methods of staining include:

a. Dye Staining

Papanicolaou staining: Harris hematoxylin; orange G6; EA50 (eosin Y, light green SF)

May-Grunwald Giemsa staining (eosin G, methylene blue)

Ziehl-Neelsen stain

Modified Ziehl Neelson (for acid fast bacilli), Gram staining (Bacteria), Mucicarmine (mucins), PAS (for glycogen, fungal wall, lipofuscin, etc), Oil red O (lipids), Perl's Prussian blue (iron), modified Fouchet's test (bilirubin), any fluorescent/non-fluorescent dye for biological molecule, organelles, cells and biological structures, for example nuclei acid dyes: cyanine dyes (PicoGreen, OliGreen and RiboGreen, SYBR Gold, SYBR Green I and SYBR Green II, CyQUANT GR dye), cyanine dimer dyes (SYTOX, POPO-1, TOTO-1, YOYO-1, BOBO-1, DOJO-1, POPO-3, LOLO-1, TOTO-3, PO-PRO-1, JO-PRO-1, YO-PRO-1, PO-PRO-3, YO-PRO-3, TO-PRO-3, TO-PRO-5), amine-reacfive cyanine dye (SYBR 101 dye), phenanthridines and acridines (ethidium bromide (EB) and ethidium homodimer-1, propidium iodide (PI), acridine orange (AO), hexidium iodide, dihydroethidium, ethidium homodimer-1, ethidium homodimer-2, ethidium monoazide, acridine homodimer bis-(6-chloro-2-methoxy-9-acridinyl)spermine, ACMA), indoles and imidazoles (Hoechst 33258, Hoechst 33342, Hoechst 34580, DAPI), 7-Aminoactinomycin D and Actinomycin D, Hydroxystilbamidine, LDS 751, Nissl Stains b. IHC/IF Staining Direct method, indirect method, PAP method (peroxidase anti-peroxidase method), Avidin-Biotin Complex (ABC) Method, Labeled StreptAvidin Biotin (LSAB) Method, Polymeric Methods (EnVision Systems based on dextran polymer technology, ImmPRESS polymerized reporter enzyme staining system), CAS system (from DAKO), CSA II—Biotin-free Tyramide Signal Amplification System c. ISH/FISH Method: direct and indirect methods Probes: double-stranded DNA (dsDNA) probes, single-stranded DNA (ssDNA) probes, RNA probes (riboprobes), synthetic oligonucleotides labelling probes: for example, DIG (digoxigenin), biotin, fluorophore (FITC, alexa, tyramide, etc.)

d. Other Materials

Acridine orange (50 ug/ml) and hematoxylin staining solution (from Vector Laboratories) were used in this study.

Sample holders. The sample holder comprises X-plate with spacers/pillars that have a substantially uniform height and a nearly uniform cross-section separated from one another by a consistent, defined distance.

For example X-Plate is 175 um thick PMMA with a pillar array of 30×40 um pillar size, 10 um pillar height and 80 um inter space distance, or iMOST Q-Card comprising X-plate with 175 um thick PMMA with a pillar array of 40 um diameter pillar size, 10 um pillar height and 120 um inter space distance.

The invention claimed is:

1. A method of staining a sample that is a tissue, comprising:
    (a) obtaining a first plate and a second plate, wherein the first and second plates are movable relative to each other to form different configurations including an open configuration and a closed configuration, the first plate is flexible, and has a plurality of spacers on its surface, wherein the spacers are pillars and have a substantially uniform height of 100 µm or less;
    (b) placing, on the second plate, the sample to be stained when the two plates are in the open configuration;
    (c) depositing a staining solution either on the first plate or the sample; and
    (d) sandwiching the sample and the staining solution between the first plate and the second plate and pressing the plates together into the closed configuration so that at least part of the staining solution is sandwiched between the sample and first plate;
    (e) imaging, without washing to remove stain solution from the sample, the thin layer of the sample between the two plates;
    wherein in the open configuration, the two plates are completely or partially separated apart, the spacing between the plates is not regulated by the spacers; and
    wherein in the closed configuration, the spacing between the plates is regulated by the plates, and the spacers.

2. A kit for staining an analyte of a sample that is a tissue, comprising: (a) a first plate and a second plate; each, on its surface, having a sample contact area for contacting the sample that contains or is suspected of containing an analyte, wherein the two plates are movable to different configurations including an open configuration and a closed configuration, the first plate is flexible and has a plurality of spacers on its surface, wherein the spacers are pillars; and (b) a staining solution that stains the analyte; wherein the distance between the two sample contact areas and the concentration of the staining solution in the thin layer are selected to make, during an imaging by an imager, the stained analyte in the thin layer is distinguishable from the rest of thin layer, wherein in the open configuration, the first and second plates are completely or partially separated apart, the spacing between the first and second plates is not regulated by the spacers; and wherein in the closed configuration, at least part of the sample is between the two plates, a layer of at least part of the staining solution is between the at least part of the sample and the first plate, and the spacing between the plates is regulated by the first and second plates and the spacers;
    an imager for imaging the stained analyte of the sample to obtain an image; and
    a non-transitory computer readable medium having encoded thereon an imaging algorithm that, when executed by a processor, cause the processor to analyze the image.

3. The method of claim 1, wherein the analyte in the sample to be stained is inside a membrane of a cell in the sample.

4. The method of claim 1, further comprising a step of quantifying whether the cell has or does not have an analyte inside the cell.

5. The method of claim 3, further comprising: (i) quantifying the cell that contains or does not contain an analyte and (ii) quantifying the percentage of the cell containing the analyte relative to the total number of the cell.

6. The method of claim 3, wherein the stain solution comprises a detection probe that specifically binds the analyte and is capable of emitting a light at a wavelength, the light emitted by the detection probe is fluorescence, and wherein the method further comprises (i) measuring the fluorescence intensity of the cell having the analyte bound to the detection probe, (ii) measuring the number of the cell having the analyte bound to the detection probe, and (iii) calculating a total fluorescence intensity by multiplying the total number of the cell having the analyte bound to the detection probe in a unit area and the average of the fluorescence intensity of the cell having the analyte bound to the detection probe.

7. The method of claim 1, wherein the sample has an initial thickness in the open configuration thicker than the final thickness in the closed configuration.

8. The method of claim 1, wherein the spacer height is 50 µm (micron) or less.

9. The method of claim 1, wherein the uniform height of the spacers is selected between 2 µm to 20 µm.

10. The method of claim 1, wherein the uniform height of the spacers is 10 µm.

11. The method of claim 1, wherein the step of the imaging of step (e) is performed 300 seconds or less after sandwiching of step (d).

12. The method of claim 1, wherein the thickness of the thin layer is selected to make some of the cell having no overlap or significant overlap with other cells in the thin layer.

13. The method of claim 1, wherein a permeabilization reagent is coated on the surface of at least one of the first and second plates.

14. The method of claim 1, wherein a permeabilization reagent is introduced to the sample before the sample and the permeabilization reagent are sandwiched between the two plates.

15. The method of claim 1, wherein one of the plates further has a dry stain reagent coated on its surface, and wherein the stain solution is a transfer liquid that transfer the dry stain agent into the sample.

16. The method of claim 1, wherein the stain solution is introduced to the sample before the sample and the permeabilization reagent are sandwiched between the two plates.

17. The method of claim 1, wherein the sample comprises bodily fluid selected from the group consisting of amniotic fluid, aqueous humour, vitreous humour, blood, breast milk, cerebrospinal fluid (CSF), cerumen (earwax), chyle, chime, endolymph, perilymph, feces, breath, gastric acid, gastric juice, lymph, mucus, pericardial fluid, peritoneal fluid, pleural fluid, pus, rheum, saliva, exhaled breath condensates, sebum, semen, sputum, sweat, synovial fluid, tears, vomit, urine, and any combination thereof.

18. The method of claim 1, wherein the stain is Papanicolaou staining comprising Harris hematoxylin, orange G6, and EA50.

19. The method of claim 1, wherein the analyte comprises a target tissue or cell.

20. The method of claim 1, wherein the analyte comprises a nucleic acid or protein.

21. The method of claim 1, wherein the distance between the two sample contact areas is less than 250 microns (µm).

22. The method of claim 1, wherein the stain is a Pap tests smear to detect cell changes caused by human papillomavirus (HPV), and wherein the distance between the two sample contact areas and the concentration of the stain solution in the thin layer are selected to make, during the imaging, the stained analyte in the thin layer is distinguishable from the rest of thin layer.

23. The method of claim 1, wherein the step of the imaging is performed 60 seconds or less after sandwiching of step (d).

24. The method of claim 1, wherein the spacer height is selected between 5 µm to 20 µm, the stain is a Pap smear to detect cell changes caused by human papillomavirus (HPV); wherein the cells are collected by a swab from a patient's cervix; and wherein the distance between the two sample contact areas and the concentration of the stain solution in the thin layer are selected to make, during the imaging, the stained analyte in the thin layer is distinguishable from the rest of thin layer.

25. The method of claim 1, wherein the stain solution comprises Ziehl-Neelsen staining, or fluorescent acid fast staining using auramine-O or auramine-rhodamine, or nucleic acid-binding dye.

26. The method of claim 25, wherein the nucleic acid-binding dye is a cyanine dye.

27. The method of claim 1, wherein the stain solution comprises an antigen retrieval agent capable of facilitating retrieval of antigen.

28. The method of claim 1, further comprising analyzing the image using machine learning, supervised machine learning, unsupervised machine learning, or reinforcement learning.

29. The method of claim 1, further comprising analyzing the image using machine learning, supervised machine learning, unsupervised machine learning, or reinforcement learning.

* * * * *